(12) United States Patent
Dacosta et al.

(10) Patent No.: US 10,959,741 B2
(45) Date of Patent: Mar. 30, 2021

(54) BONE FIXATION SYSTEM, ASSEMBLY, DEVICES, INSERTION GUIDES, AND METHODS OF USE

(71) Applicant: Paragon 28, Inc., Englewood, CO (US)

(72) Inventors: Albert Dacosta, Lone Tree, CO (US); Joseph Dogué, Aurora, CO (US); Frank Barmes, Littleton, CO (US); Randy Allard, Golden, CO (US)

(73) Assignee: Paragon 28, Inc., Englewood, CO (US)

( * ) Notice: Subject to any disclaimer, the term of this patent is extended or adjusted under 35 U.S.C. 154(b) by 187 days.

(21) Appl. No.: 15/942,074

(22) Filed: Mar. 30, 2018

(65) Prior Publication Data
US 2018/0289379 A1 Oct. 11, 2018

Related U.S. Application Data

(63) Continuation of application No. PCT/US2018/025454, filed on Mar. 30, 2018.
(Continued)

(51) Int. Cl.
*A61B 17/17* (2006.01)
*A61B 17/72* (2006.01)
(Continued)

(52) U.S. Cl.
CPC ...... *A61B 17/1775* (2016.11); *A61B 17/1725* (2013.01); *A61B 17/7291* (2013.01);
(Continued)

(58) Field of Classification Search
CPC .................................................. A61B 17/1775
See application file for complete search history.

(56) References Cited

U.S. PATENT DOCUMENTS 4,312,337 A * 1/1982 Donohue ........... A61B 17/1796
606/103
5,624,447 A * 4/1997 Myers ................ A61B 17/1717
606/104
(Continued)

FOREIGN PATENT DOCUMENTS

ZA          200601343          4/2007

OTHER PUBLICATIONS

International Preliminary Report on Patentability for International Application No. PCT/US2018/025454, dated Oct. 1, 2019, 12 pages, International Bureau of WIPO.
(Continued)

*Primary Examiner* — Nicholas W Woodall
(74) *Attorney, Agent, or Firm* — Heslin Rothenberg Farley & Mesiti P.C.; Jacquelyn A. Graff, Esq.

(57) ABSTRACT

Guides, devices, instruments, and systems for fixing a fractured bone are disclosed. An insertion guide includes a handle member and a guide member coupled to a second end of the handle member. The guide member being curved relative to the longitudinal axis of the handle member. A bone fixation system including an insertion guide, a guide wire and a fastener. The insertion guide including a handle member and a guide member coupled to an end of the handle member. The guide member being curved and including a through hole for receiving the guide wire. The fastener including a cannulation for receiving the guide wire. Methods of using a bone fixation systems for fixing fractured bones are also disclosed.

19 Claims, 30 Drawing Sheets

Related U.S. Application Data

(60) Provisional application No. 62/479,535, filed on Mar. 31, 2017.

(51) Int. Cl.
*A61B 17/86* (2006.01)
*A61B 17/00* (2006.01)

(52) U.S. Cl.
CPC ......... *A61B 17/7233* (2013.01); *A61B 17/864* (2013.01); *A61B 17/8625* (2013.01); *A61B 2017/0046* (2013.01)

(56) References Cited

U.S. PATENT DOCUMENTS

| | | | |
|---|---|---|---|
| D398,996 S * | 9/1998 | Simmons | A61F 2/30771 D24/140 |
| 6,074,392 A * | 6/2000 | Durham | A61B 17/1717 606/62 |
| 6,419,678 B1 * | 7/2002 | Asfora | A61B 17/1757 606/96 |
| 9,936,995 B2 * | 4/2018 | Dacosta | A61B 17/56 |
| 2008/0086144 A1 | 4/2008 | Zander | |
| 2012/0078252 A1 * | 3/2012 | Huebner | A61B 17/1728 606/70 |
| 2012/0197259 A1 | 8/2012 | Smith | |
| 2012/0203290 A1 | 8/2012 | Warren et al. | |
| 2012/0265205 A1 | 10/2012 | Steiner et al. | |
| 2012/0330321 A1 | 12/2012 | Johnson et al. | |
| 2013/0150903 A1 * | 6/2013 | Vincent | A61B 17/86 606/301 |
| 2014/0031935 A1 | 1/2014 | Donner | |
| 2014/0277196 A1 | 9/2014 | Foley | |
| 2015/0112353 A1 | 4/2015 | Jerke et al. | |
| 2015/0359580 A1 * | 12/2015 | Dacosta | A61B 17/17 606/281 |
| 2017/0007307 A1 | 1/2017 | Cocaign et al. | |
| 2018/0021145 A1 * | 1/2018 | Seavey | A61F 2/30771 438/419 |

OTHER PUBLICATIONS

International Search Report and Written Opinion of the International Searching Authority for PCT/US2018/025454, dated Aug. 8, 2018, 15 pages.

Extended European Search Report issued in corresponding European Patent Application No. 18774296.0, dated Jan. 14, 2021, 7 pages.

* cited by examiner

BONE FIXATION SYSTEM, ASSEMBLY, DEVICES, INSERTION GUIDES, AND METHODS OF USE

CROSS REFERENCE TO RELATED APPLICATION

This application is a continuation of PCT Application No. PCT/US2018/025454 filed on Mar. 30, 2018, which claims priority benefit under 35 U.S.C. § 119(e) of U.S. provisional application No. 62/479,535 filed Mar. 31, 2017, which is incorporated herein by reference in its entirety.

TECHNICAL FIELD

The present disclosure relates generally to general, podiatric, and orthopaedic surgery related to fixation of fractured bones. More specifically, but not exclusively, the present disclosure relates to guides, devices, instruments, systems and methods for fixing a fractured bone.

BACKGROUND OF THE INVENTION

Most solutions for fractures in the proximal fifth metatarsal, such as, Jones fractures, involve the placement of a lateral plate or a central fixation screw. Generally, plates are used because of the ease of surgical access. In addition, plates are generally easier to use for avulsion fractures of the fifth metatarsal tuberosity. However, using a plate may result in an uncomfortable prominence for the patient. In addition, in some circumstances plating techniques do not provide optimal stability which may be found with central fixation of an intramedullary screw. An intramedullary screw may be placed through the central axis and in the intramedullary canal of the fifth metatarsal. The currently used intramedullary screw approach, however, may be hampered or rendered impossible by difficulty in accessing the central axis and/or by approach conflicts with the lateral malleolus, i.e. ankle, as well as soft tissue irritation. Thus, new and improved bone fixation systems, assemblies, insertion guides, and methods for inserting an intramedullary screw are needed which improve the stability of the patient's foot during healing and after fusion.

SUMMARY OF THE INVENTION

The present disclosure is directed toward devices and methods for use in fixation of a fracture. The insertion guides provide an orientation for insertion of a fixation screw into the central axis of a bone, such as, the fifth metatarsal, and across a patient's fracture.

In one aspect of the present disclosure provided herein, is a bone fixation system. The bone fixation system including an insertion guide, a guide wire, and a fastener. The insertion guide has a handle member and a guide member coupled to an end of the handle member. The guide member is curved and has a through hole for receiving the guide wire. The fastener has a cannulation for receiving the guide wire.

In another aspect of the present disclosure provided herein, is an insertion guide. The insertion guide including a handle member and a guide member coupled to a second end of the handle member. The guide member being curved relative to the longitudinal axis of the handle member.

In yet another aspect of the present disclosure provided herein, is a method of using a bone fixation system for fixation of a fifth metatarsal fracture. The method includes creating an incision near the fifth metatarsal and aligning a guide member of an insertion guide with the central axis of the fifth metatarsal. The method also includes inserting an alignment wire through the guide member and into the central axis of the fifth metatarsal and removing the insertion guide from the alignment wire. The method further includes inserting a fastener over the alignment wire and into the central axis of the fifth metatarsal and removing the alignment wire from the fifth metatarsal. Finally, the method includes closing the incision.

In a further aspect of the present disclosure provided herein, is a method of using a bone fixation system for fixation of a fifth metatarsal. The method includes creating an incision near the fifth metatarsal and inserting a pivoting member into the fifth metatarsal. The method also includes coupling an alignment guide to the pivoting member and aligning a guide sleeve of the alignment guide with the central axis of the fifth metatarsal. The method further includes inserting a guide wire through the guide sleeve and into the central axis of the fifth metatarsal and removing the alignment guide from the pivoting member and the pivoting member from the fifth metatarsal. Finally, the method includes inserting a fastener over the guide wire and into the central axis of the fifth metatarsal and closing the incision.

In another aspect of the present disclosure provided herein, is a method of using a bone fixation system for fixation of a fifth metatarsal. The method includes creating an incision near the fifth metatarsal and obtaining an insertion guide. The method also includes determining a desired curvature of a guide member of the insertion guide and pressing a tab of the insertion guide to activate a pulling member to curve the guide member. The method further includes securing the guide member at the desired curvature and aligning the guide member of the insertion guide with the central axis of the fifth metatarsal. In addition, the method includes inserting an alignment wire through the guide member and into the central axis of the fifth metatarsal and removing the insertion guide from the alignment wire. The method also includes inserting a fastener over the alignment wire and into the central axis of the fifth metatarsal and removing the alignment wire from the fifth metatarsal. Finally, the method includes closing the incision.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

DETAILED DESCRIPTION FOR CARRYING OUT THE INVENTION

Figure 1:
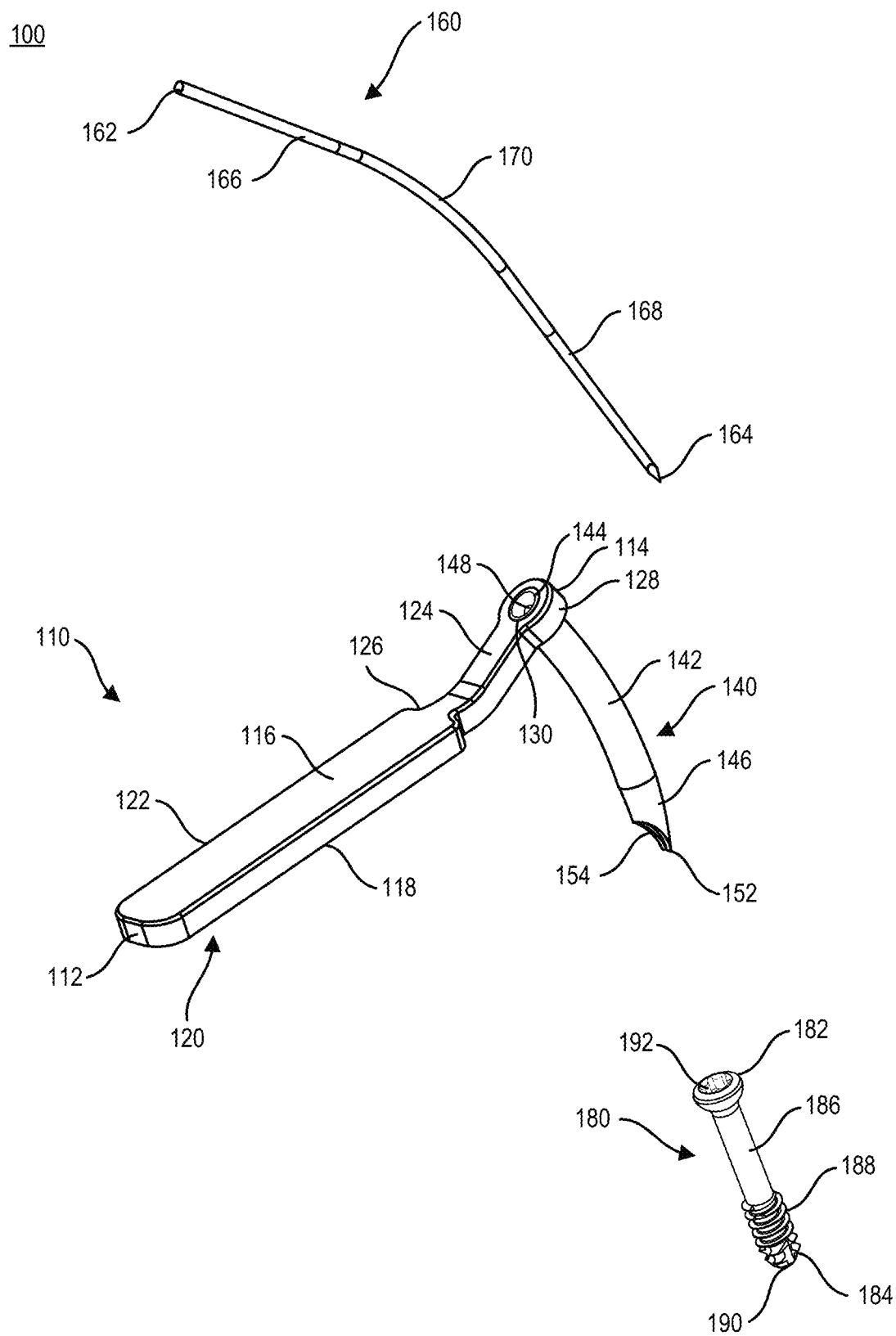
FIG. 1 is an exploded top perspective view of one embodiment of a bone fixation system, in accordance with an aspect of the present disclosure.

Generally stated, disclosed herein are guides, devices, instruments, and systems for fracture fixation. Further, methods for using the guides, devices, instruments, systems to fix a fractured bone are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation and methods are described herein with reference to use with the bones of the foot, the bones of the foot, ankle and lower leg may be used to describe the surfaces, positions, directions or orientations of the implants, devices, instrumentation and methods. Further, the implants, devices, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the implants, devices, instrumentation and methods, and the aspects, components, features and the like thereof, described herein with respect to the right foot may be mirrored so that they likewise function with the left foot. Further, the implants, devices, instrumentation and methods, and the aspects, components, features and the like thereof, disclosed herein are described with respect to the foot for brevity purposes, but it should be understood that the implants, devices, instrumentation and methods may be used with other bones of the body having similar structures.

Referring to the drawings, wherein like reference numerals are used to indicate like or analogous components throughout the several views, and with particular reference to FIGS. 1-18, there is illustrated an exemplary embodiment of a bone fixation system 100. The bone fixation system 100 includes an insertion guide 110, a k-wire 160 and a fastener 180. The insertion guide 110 may include a handle member or handle portion 120 coupled to a guide member 140, as shown in FIGS. 3-16. The handle member 120 of the insertion guide 110 may include a first end 112 opposite a second end 114 and a first surface 116 opposite the second surface 118. The guide member 140 may couple to the handle member 120 at the second end 114 and extend away from a second surface 118 of the handle member 120.

Figure 3:
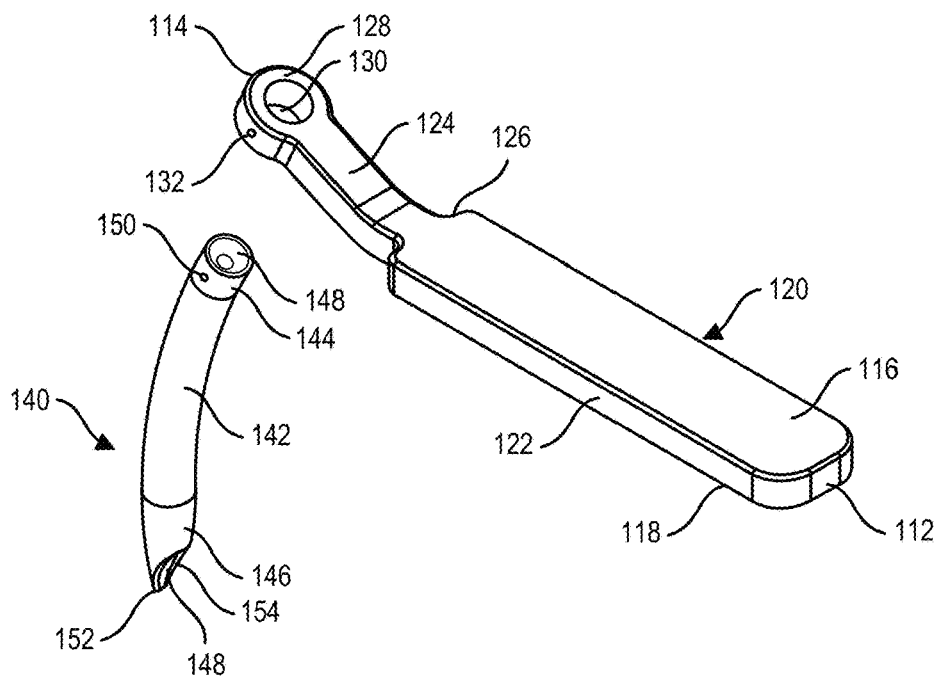
FIG. 3 is an exploded top perspective view of an insertion guide of the bone fixation system of FIG. 1, in accordance with an aspect of the present disclosure.
Figure 4:
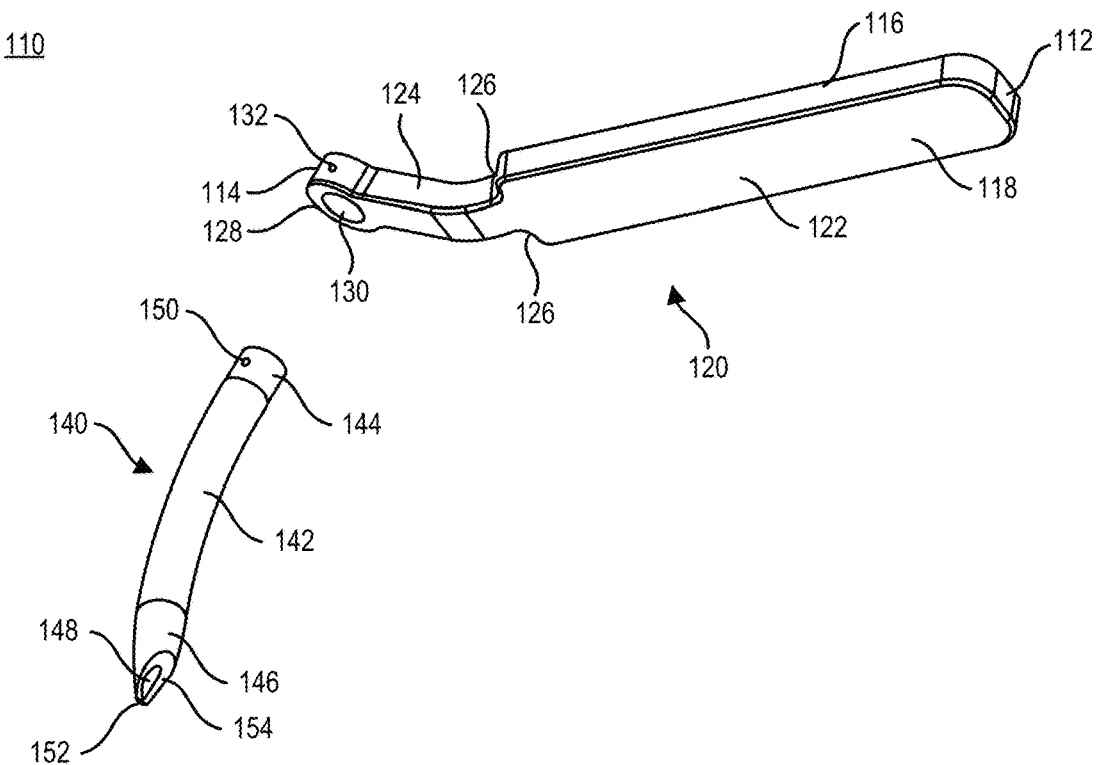
FIG. 4 is an exploded bottom perspective view of the insertion guide of FIG. 3, in accordance with an aspect of the present disclosure.
Figure 5:
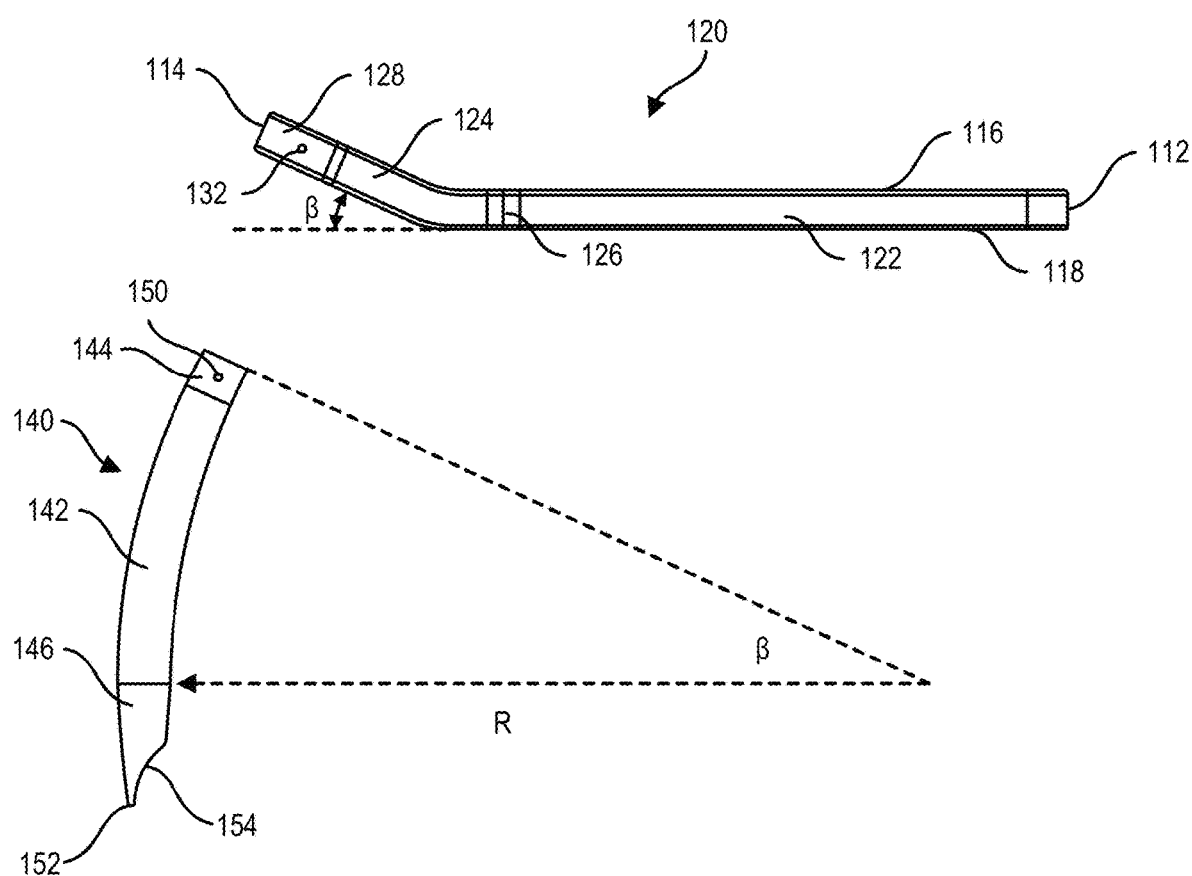
FIG. 5 is an exploded side view of the insertion guide of FIG. 3, in accordance with an aspect of the present disclosure.
Figure 6:
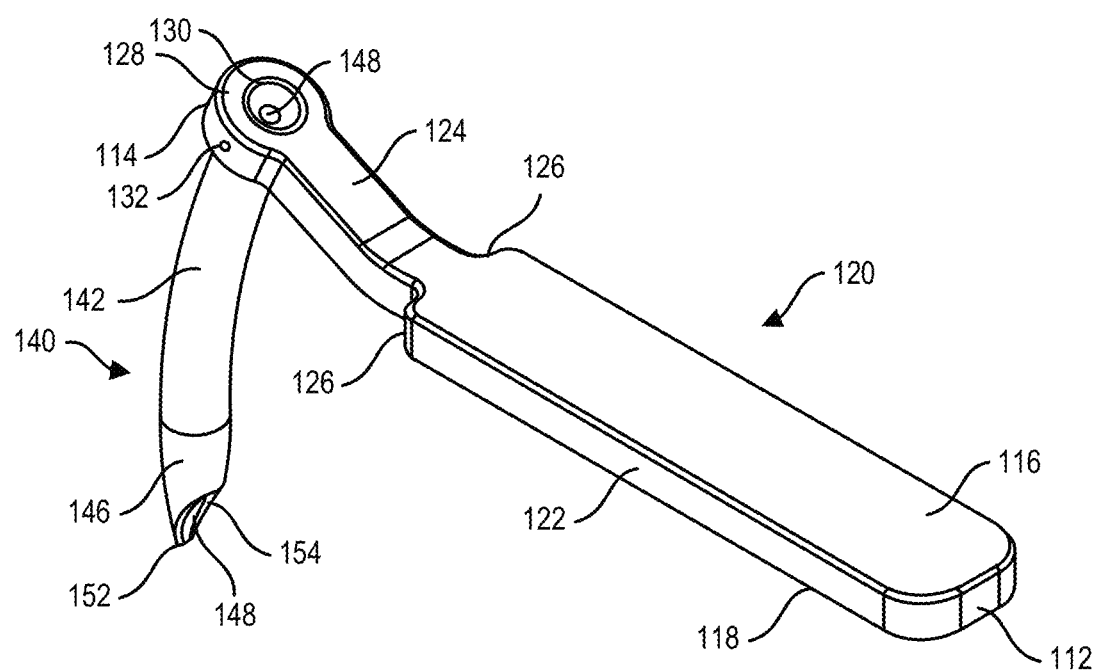
FIG. 6 is a top perspective view of the insertion guide of FIG. 3, in accordance with an aspect of the present disclosure.
Figure 7:
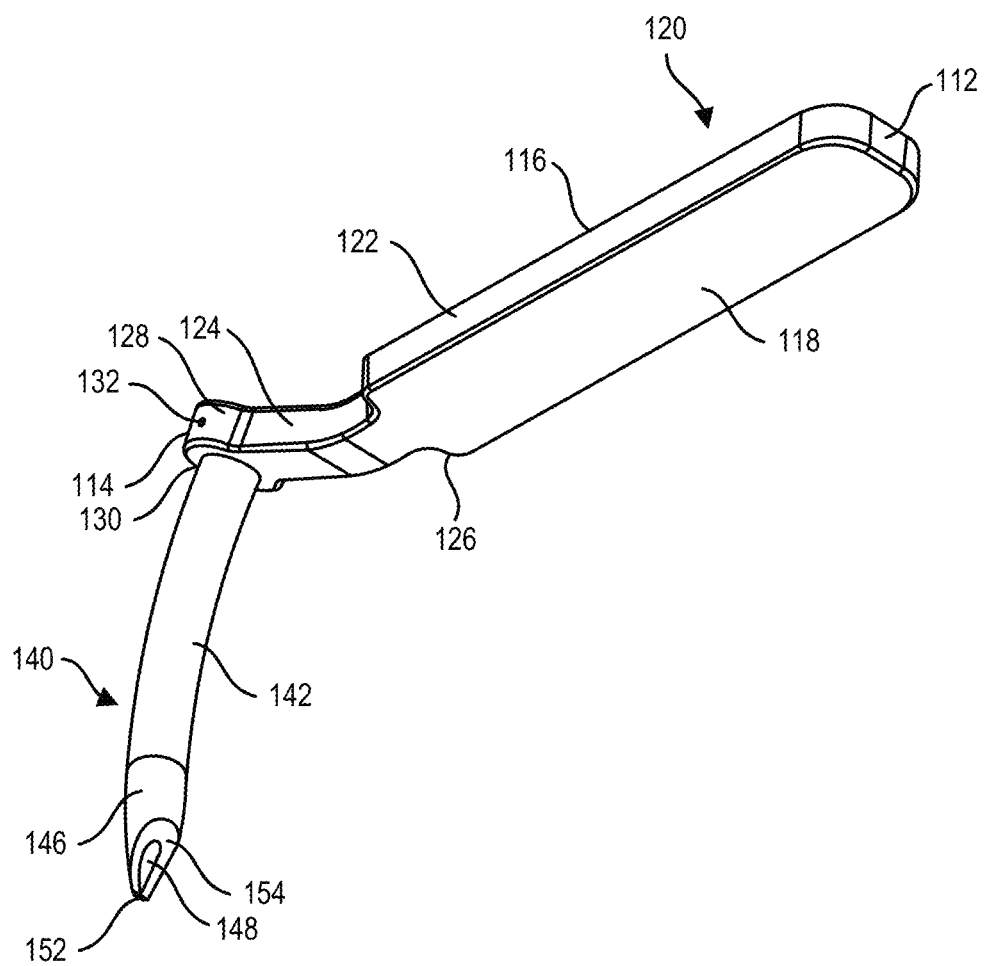
FIG. 7 is a bottom perspective view of the insertion guide of FIG. 3, in accordance with an aspect of the present disclosure.
Figure 8:
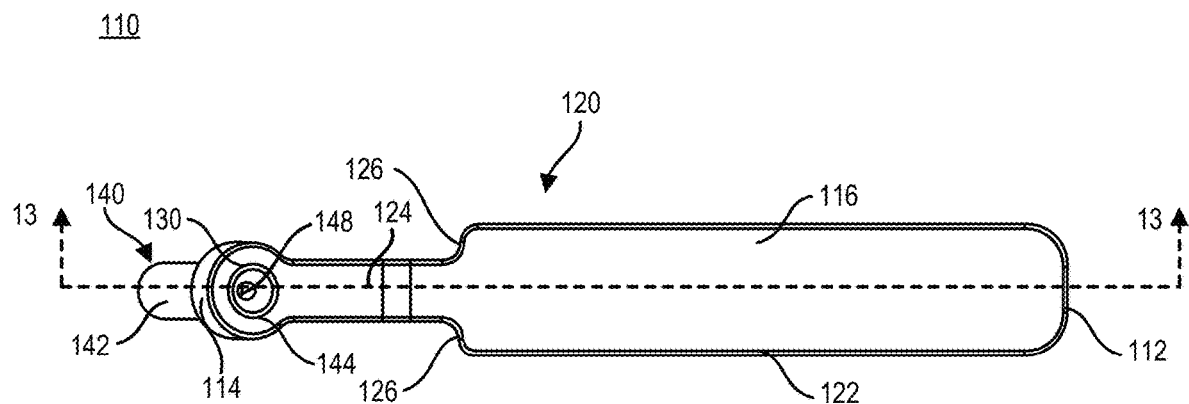
FIG. 8 is a top view of the insertion guide of FIG. 3, in accordance with an aspect of the present disclosure.
Figure 9:
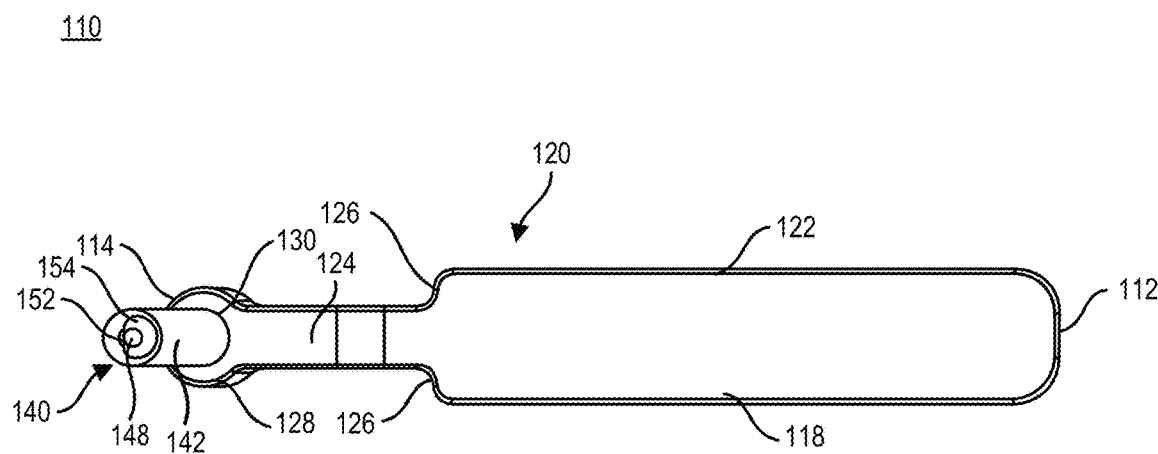
FIG. 9 is a bottom view of the insertion guide of FIG. 3, in accordance with an aspect of the present disclosure.
Figure 10:
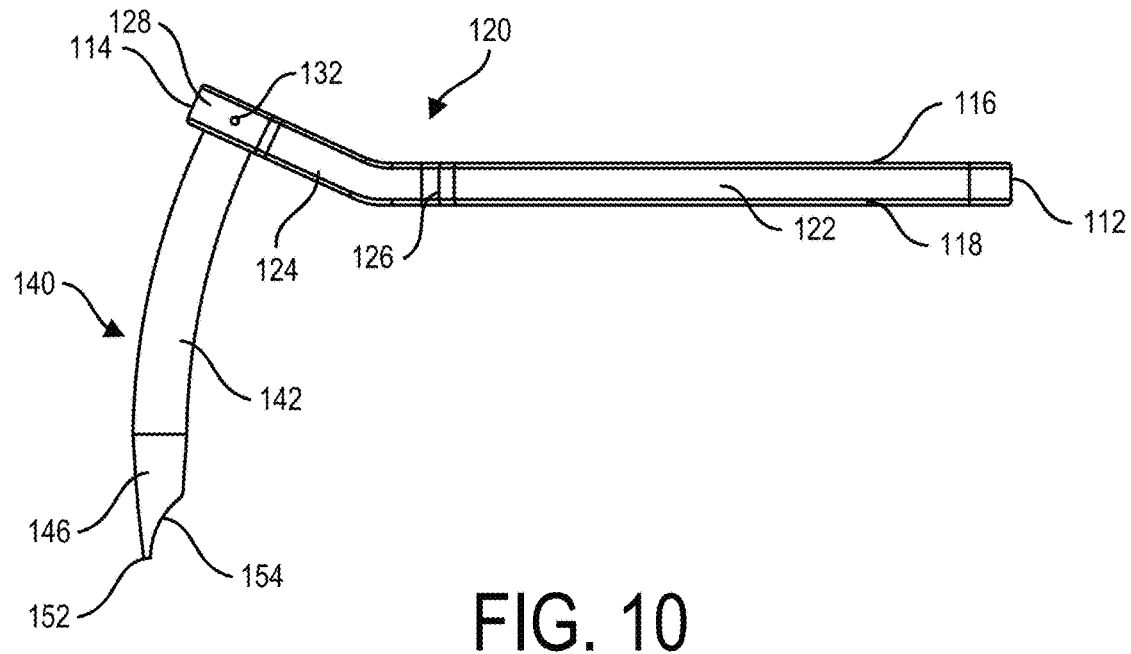
FIG. 10 is a first side view of the insertion guide of FIG. 3, in accordance with an aspect of the present disclosure.
Figure 11:
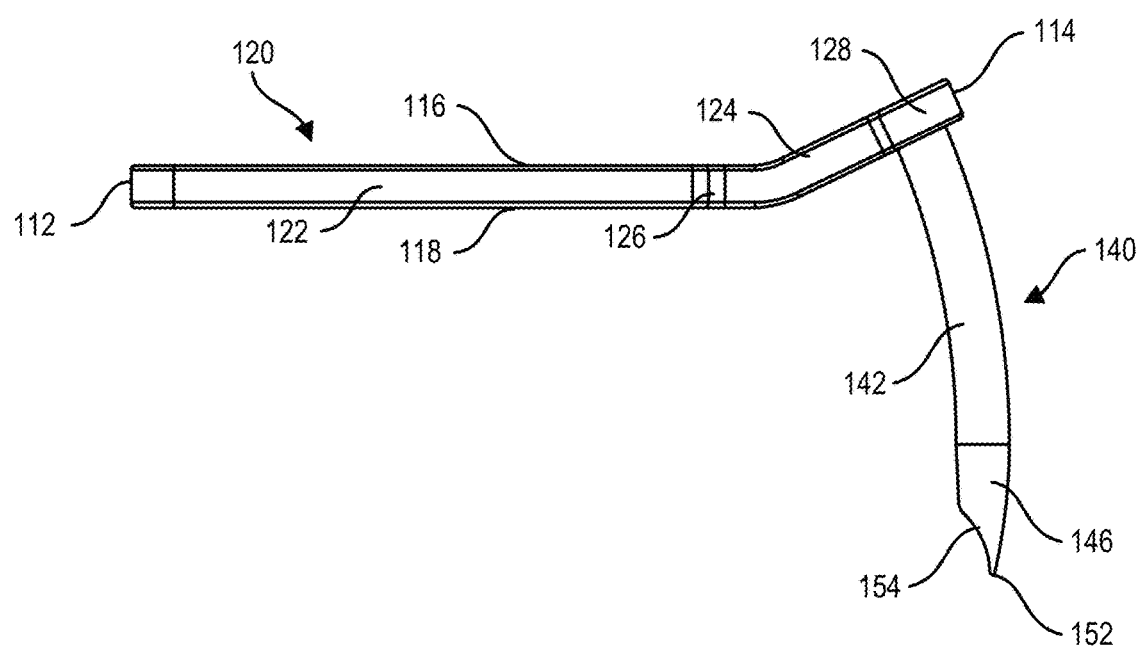
FIG. 11 is a second side view of the insertion guide of FIG. 3, in accordance with an aspect of the present disclosure.
Figure 12B:
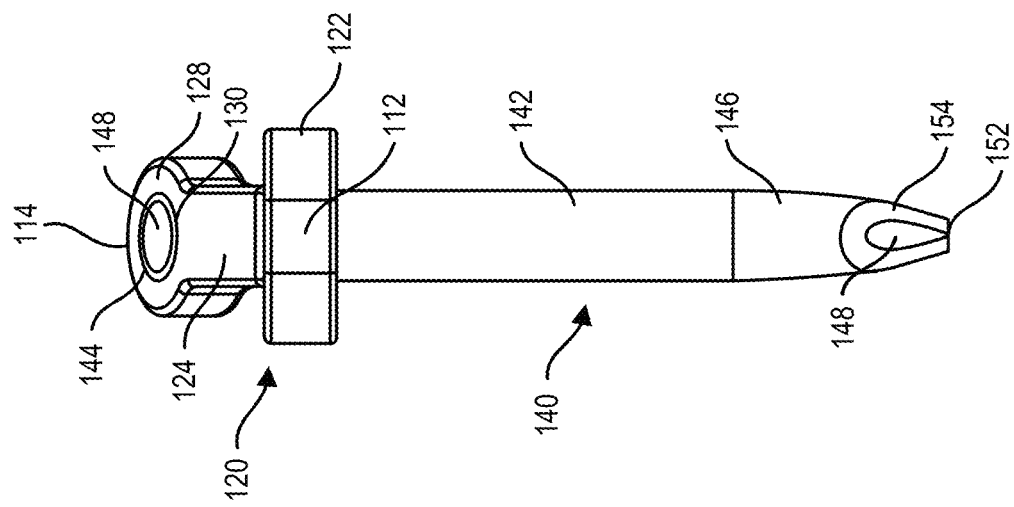
FIG. 12B is a first end view of the insertion guide of FIG. 3, in accordance with an aspect of the present disclosure.
Figure 12A:
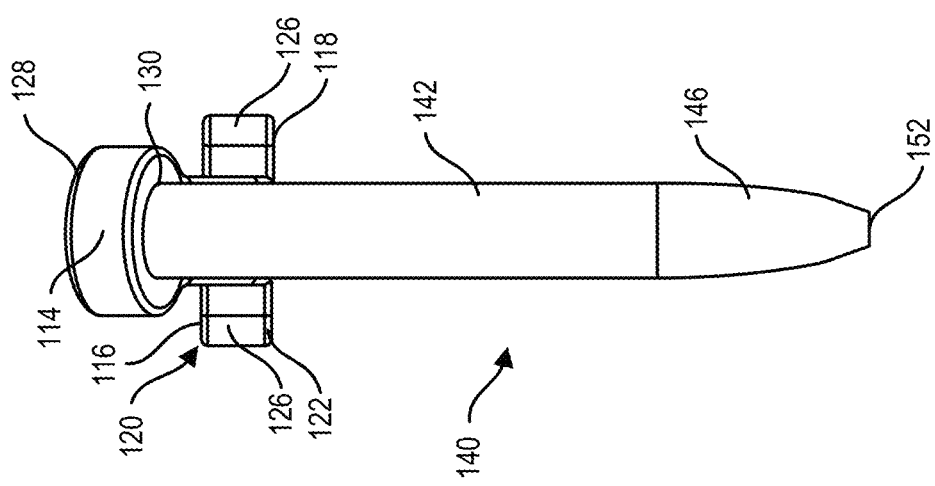
FIG. 12A is a second end view of the insertion guide of FIG. 3, in accordance with an aspect of the present disclosure.

As shown in FIGS. 3-5, the handle member 120 may include a body 122 and an alignment member 124. The body 122 may be coupled to the alignment member 124 by a neck or tapered region 126. The sides of the neck region 126 may be, for example, tapered or curved between the wider body portion 122 and the narrower alignment member 124. The handle member 120 may also include an angle or curve β positioned at the neck region 126 to angle the alignment member 124 relative to the body 122, as shown in FIG. 5. The alignment member 124 may be angled relative to the body 122 by angle β. The angle β may be, for example, approximately 0-30 degrees, more specifically, approximately 25 degrees. It is also contemplated that the handle member 120 may not have an angle β and may be, for example, flat along the length of the handle member 120.

The alignment member 124 may have an attachment portion 128 positioned at the second end 114. The attachment portion 128 may include an opening 130 sized and shaped or configured to receive an end of the guide member 140. The opening 130 may extend through the attachment portion 128 of the alignment member 124 from the first surface 116 through the second surface 118. The attachment portion 128 may also include a fastener hole 132, as shown in FIGS. 2-7 and 10. The fastener hole 132 may extend from an exterior surface through the attachment portion 128 and into the opening 130. The fastener hole 132 may receive a fastener (not shown) to secure the guide member 140 to the handle member 120, as shown in FIGS. 2-7 and 10.

Figure 13:
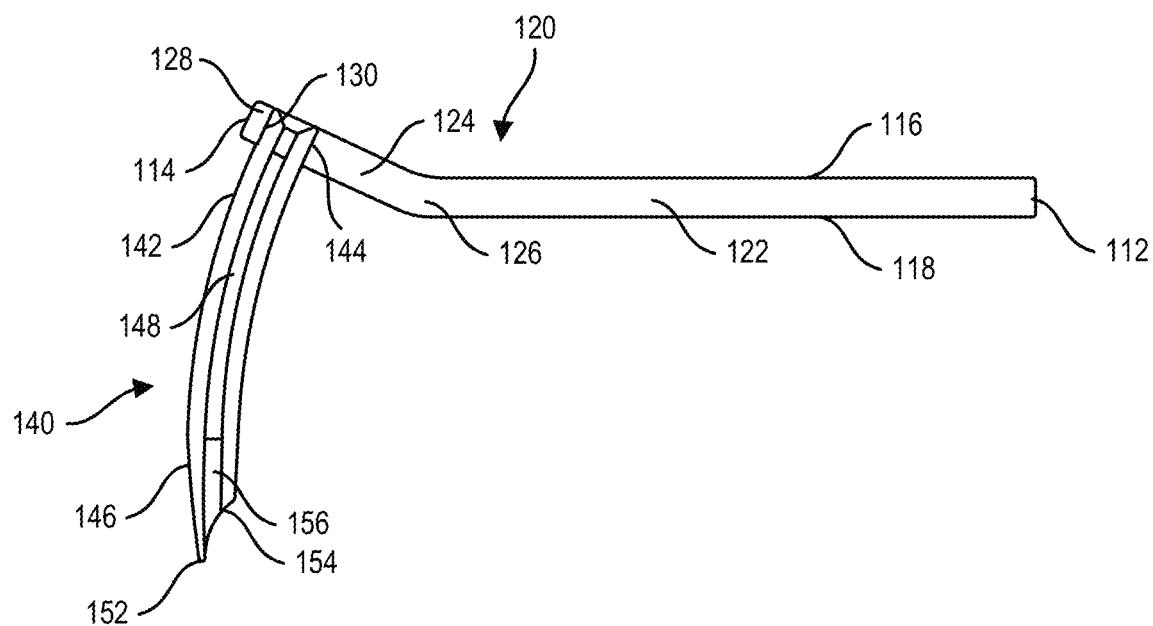
FIG. 13 is a cross section of the insertion guide of FIG. 3 taken along line 13-13 in FIG. 8, in accordance with an aspect of the present disclosure.

As shown in FIGS. 3-5, the guide member 140 includes a guide body 142 with an engagement portion or coupling member 144 at a first end and a bone contacting member or portion 146 at a second end. The guide member 140 may have an angle or curve β. As noted above, the angle β may be, for example, approximately 0-30 degrees, more specifically, approximately 25 degrees. The guide member 140 may also have a radius of curvature R. The radius of curvature R of the guide member 140 may, for example, correspond to the length of the alignment member 124 from the angle to a center of the opening 130. Alternatively, the radius of curvature R of the guide member 140 may be, for example, larger or smaller than the length of the alignment member 124 from the angle to a center of the opening 130. The guide body 142 may have a first diameter and the engagement portion 144 may have a second diameter. The second diameter may be, for example, smaller than the first diameter. The second diameter may also be sized to correspond with the size of the opening 130 in the handle member 120. The guide member 140 may also include a through hole or cannulation 148 extending through the entire length of the guide member 140. As shown in FIG. 13, the cannulation 148 may be curved from the opening in the engagement portion 144 to the bone contacting member 146 and may have a straight portion 156 extending through the bone contacting member 146. The portion 156 may extend, for example, generally perpendicular to the body portion 122 of the handle member 120. The guide member 140 may also include a fastener hole 150, as shown in FIGS. 3-5. The fastener hole 150 may extend from an exterior surface through the engagement portion 144 and into the through hole 148. The fastener hole 150 may be aligned with the fastener hole 132 to receive the fastener (not shown). The fastener (not shown) may extend through the fastener hole 132 of the handle member 120 and the fastener hole 150 of the guide member 140 to secure the guide member 140 to the handle member 120.

Figure 14:
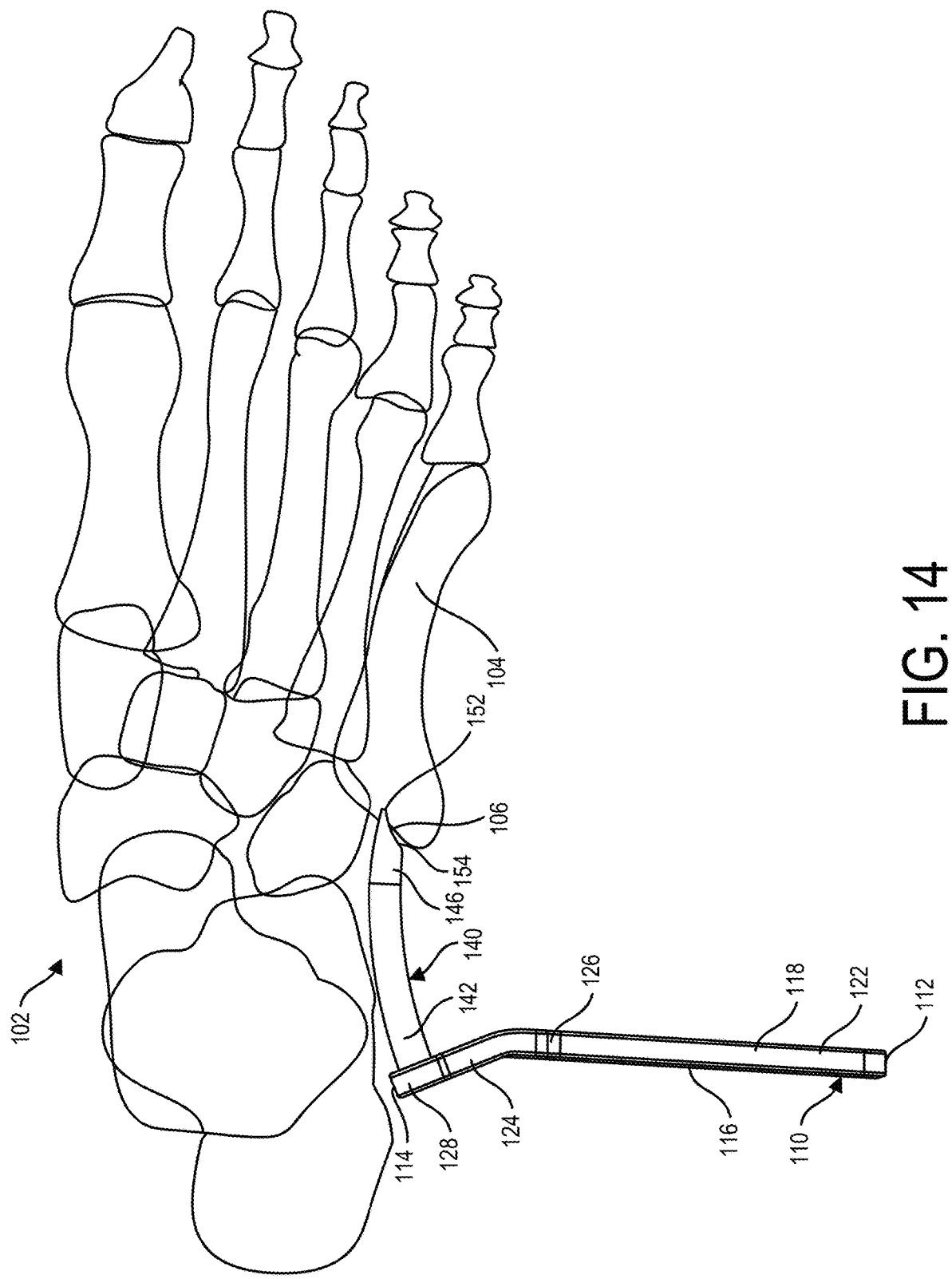
FIG. 14 is a dorsal perspective view of the insertion guide of FIG. 3 positioned with respect to a patient's foot, in accordance with an aspect of the present disclosure.
Figure 15:
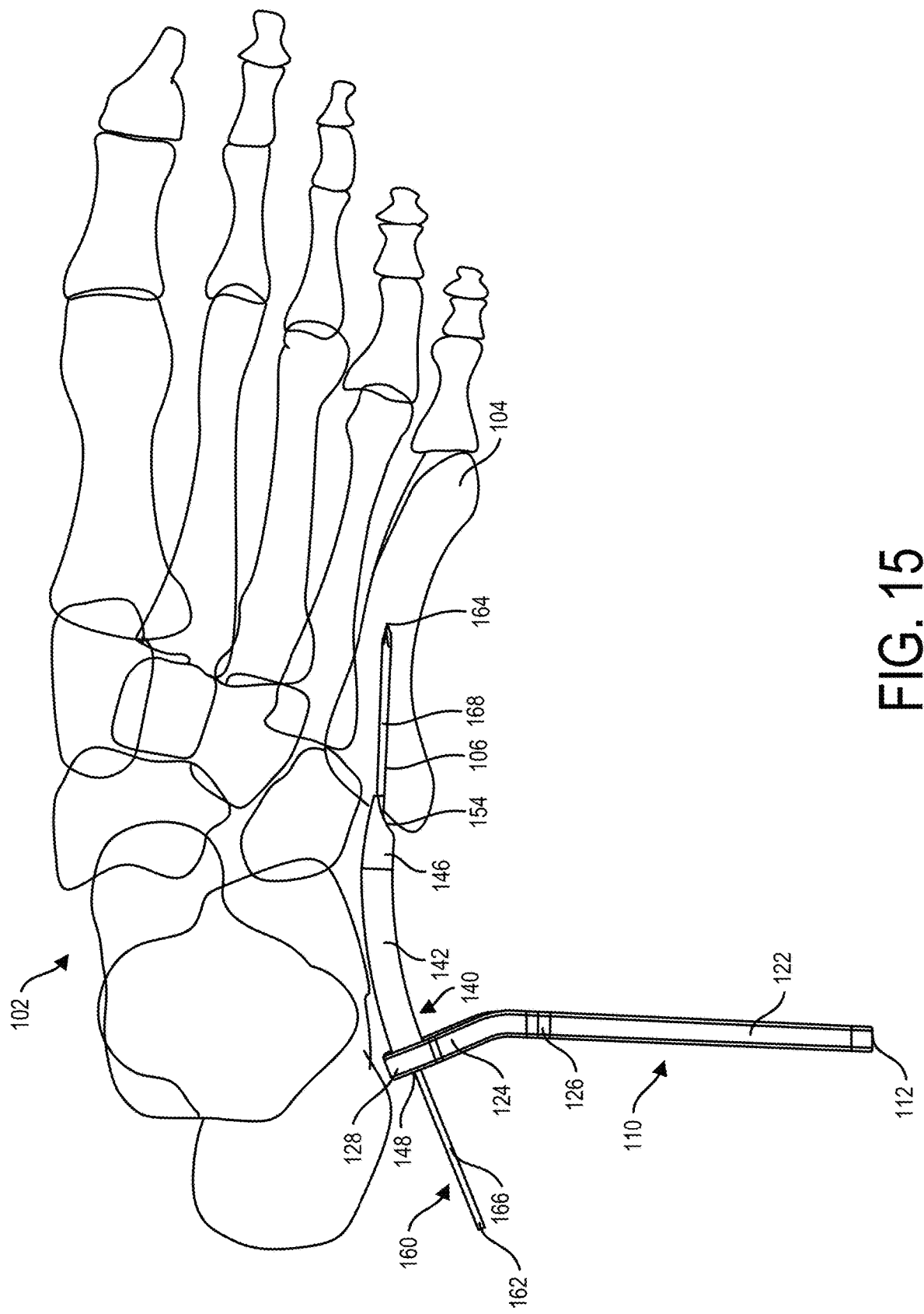
FIG. 15 is a dorsal perspective view of the insertion guide and guide wire of the bone fixation system of FIG. 1 positioned with respect to the patient's foot, in accordance with an aspect of the present disclosure.
Figure 16:
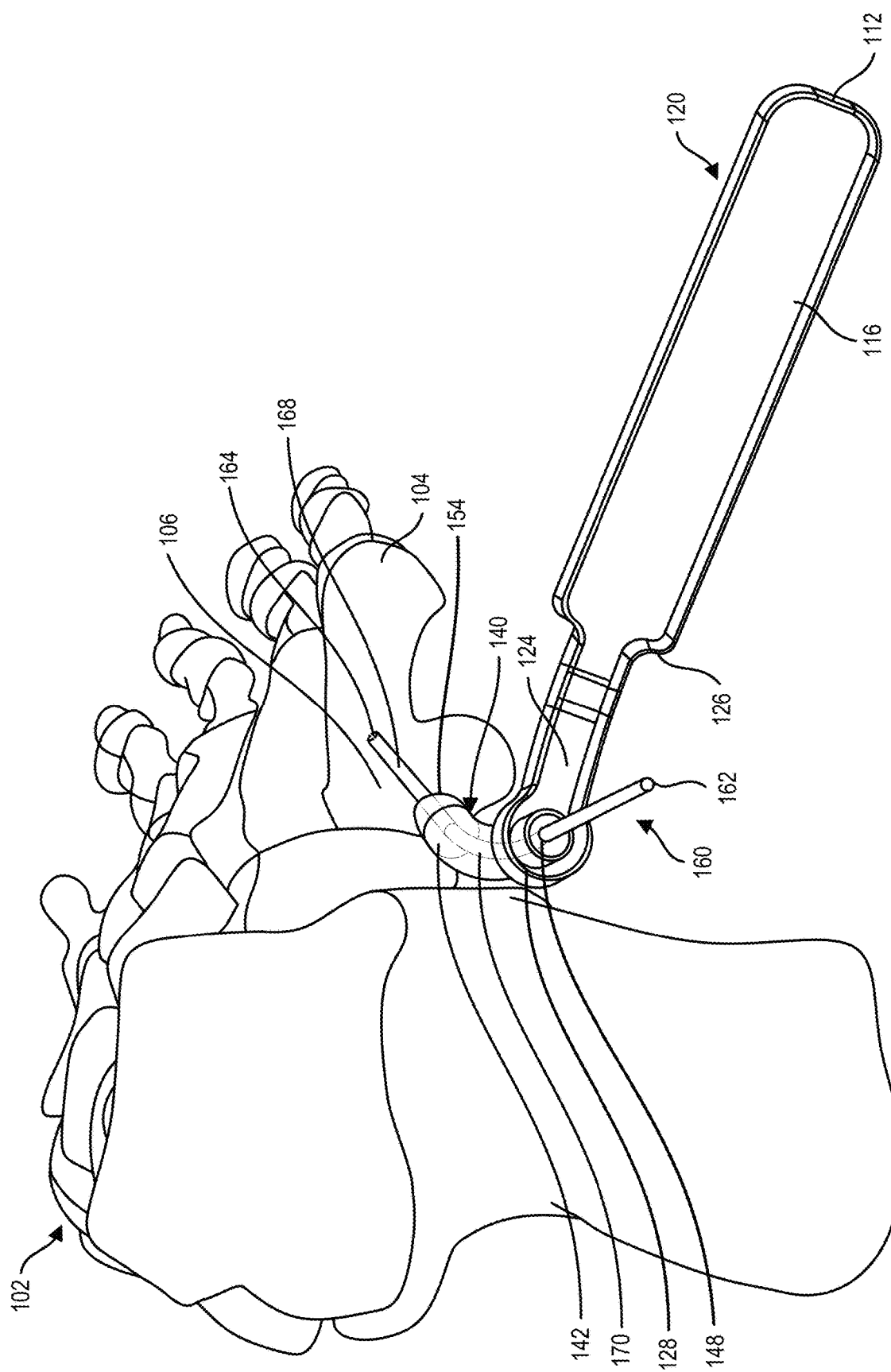
FIG. 16 is a posterior view of the patient's foot with the insertion guide and guide wire of FIG. 15, in accordance with an aspect of the present disclosure.

The bone contacting member 146 of the guide member 140 may include a tip 152 and a bone contacting surface 154, as shown in FIGS. 3-7 and 9-13. The bone contacting surface 154 may be, for example, curved to match a portion of the exterior surface of a bone. For example, the bone contacting surface 154 may be shaped to match a portion of the exterior surface of the fifth metatarsal 104 to align the through hole 148 with the central axis of the shaft 106 of the fifth metatarsal 104, as shown in FIGS. 14-16. In one embodiment, the curvature of the bone contacting surface 154 may be, for example, approximately 5 mm to 29 mm, more specifically, approximately 9 mm. As shown in FIGS. 15 and 16, the guide member 140 may also be sized and shaped or configured to receive a curved k-wire or guide wire 160.

Figure 2:
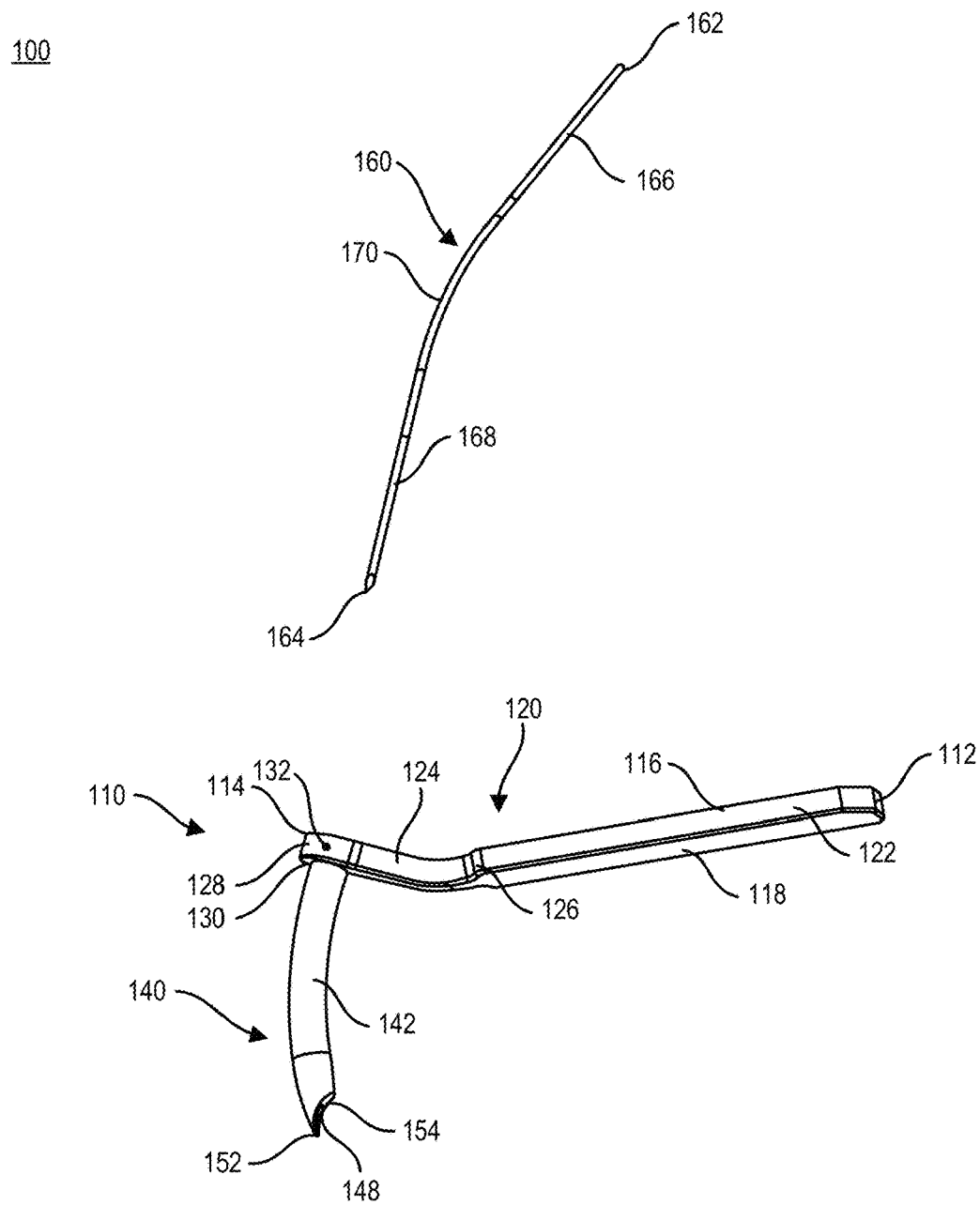
FIG. 2 is an exploded side perspective view of the bone fixation system of FIG. 1, in accordance with an aspect of the present disclosure.
Figure 2:
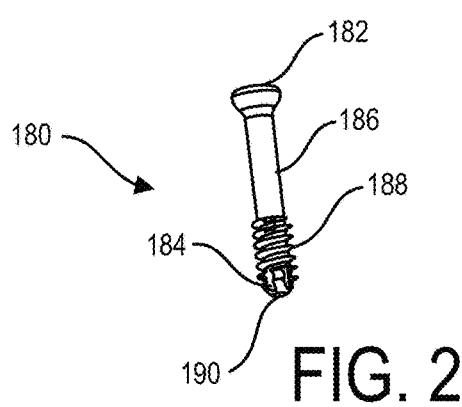

The k-wire, guide wire, or alignment wire 160, as shown in FIGS. 1 and 2, may include a first end 162 and a second end 164. The guide wire 160 may be a straight wire made of a flexible or deformable material, for example, nitinol, to allow the guide wire 160 to bend as the wire 160 follows the through hole 148 through the guide member 140. Once inserted into the through hole 148, the guide wire 160 may deform to the shape shown in FIGS. 1 and 2 and include a first wire portion 166 extending from the first end 162 to a curved portion 170. In addition, when inserted into the guide member 140, the guide wire 160 may include a second wire portion 168 extending from the curved portion 170 to the second end 164. The curved portion 170 may curve or angle the first wire portion 166 relative to the second wire portion 168 to correspond to the curvature of the through hole 148 of the guide member 140.

Figure 17:
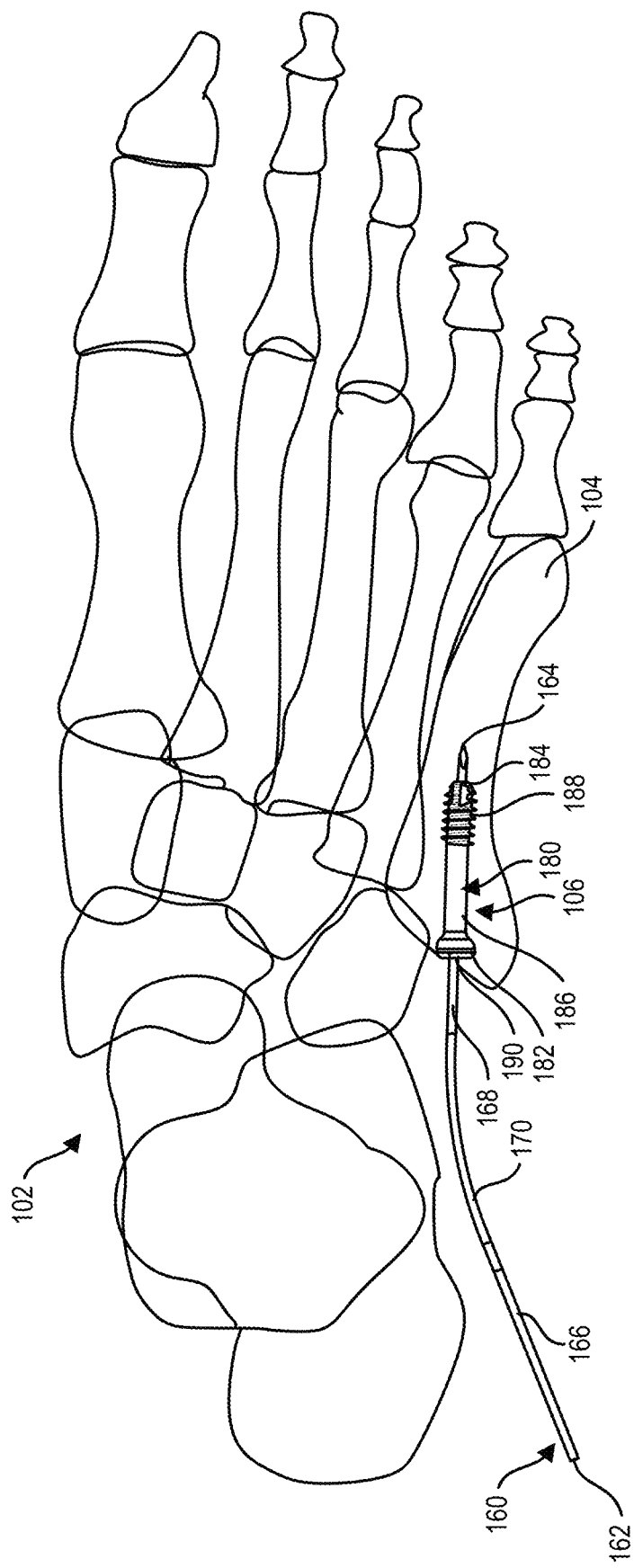
FIG. 17 is a dorsal perspective view of the guide wire and fastener of the bone fixation system of FIG. 1 positioned with respect to the patient's foot, in accordance with an aspect of the present disclosure.

As shown in FIGS. 1 and 2, the fastener, bone screw, or fixation member 180 of the bone fixation system 100 may include a head 182 at a first end and an insertion tip or end 184 at a second end. The fastener 180 may have a shank 186 extending between the head 182 and the insertion tip 184. The shank 186 may include a threaded portion 188 for engaging the bone, for example, the shaft 106 of the fifth metatarsal 104. The fastener 180 may also include a cannulation or through hole 190 extending through the fastener 180. As shown in FIG. 17, the cannulation 190 of the fastener 180 may engage the guide wire 160 for inserting the fastener 180 into a patient's bone, for example, the fifth metatarsal 104. Further, the fastener 180 may also include a drive opening 192 in the head 182 for inserting or driving the fastener 180 into the patient's bone, for example, the fifth metatarsal 104 of the patient's foot 102.

Figure 18:
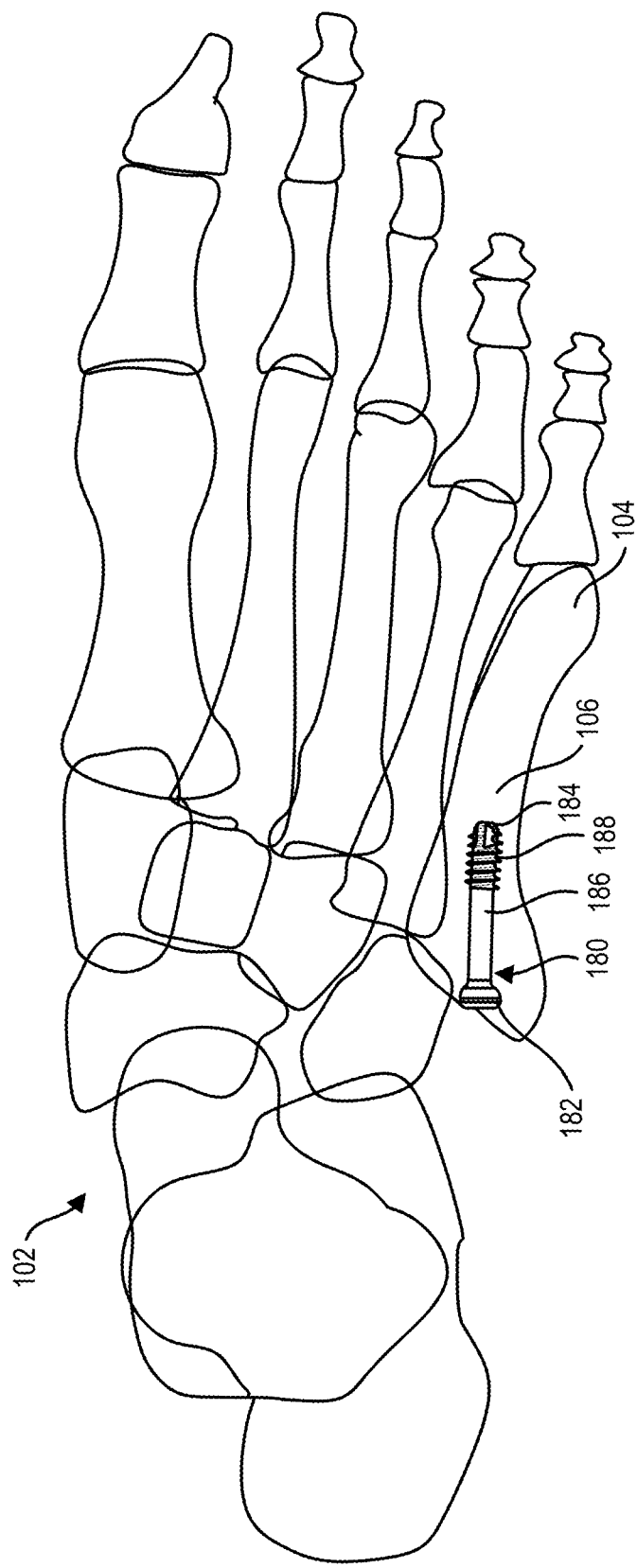
FIG. 18 is a dorsal perspective view of the patient's foot after the guide wire of FIG. 17 is removed from the inserted fastener of the bone fixation system of FIG. 1, in accordance with an aspect of the present disclosure.

A method of using the bone fixation system 100 is shown in FIGS. 14-18. As shown in FIG. 14, the assembled insertion guide 110 may be positioned on the fifth metatarsal 104 of a patient's foot 102. The bone contacting surface 154 of the guide member 140 may be positioned on the surface of the fifth metatarsal 104 to align the through hole 148 with the shaft or central axis 106 of the fifth metatarsal 104. Next, as shown in FIGS. 15 and 16, the k-wire 160 is inserted into and through the through hole 148 in the guide member 140 and into the fifth metatarsal 104. After the k-wire 160 is inserted into the fifth metatarsal 104 and placement or positioning is confirmed, the insertion guide 110 may be removed from the patient's foot 102, as shown in FIG. 17. Then, the fastener 180 may be inserted over the curved k-wire 160 and into the shaft 106 of the fifth metatarsal 104, as also shown in FIG. 17. Next, the k-wire 160 may be removed from the fastener 180 and the patient's foot 102 leaving the fastener 180 positioned in the fifth metatarsal 104, as shown in FIG. 18. The fastener 180 may be positioned to cross the fracture of the fifth metatarsal 104 to assist with fusion. Finally, the procedure may be completed and the patient's incision may be closed.

Referring now to FIGS. 19-30, another bone fixation system 200 is shown. The bone fixation system 200 may include an alignment guide or polyaxial targeting guide 210, a pivoting member 280, a guide sleeve 300, and a k-wire or guide wire 320, as shown in FIGS. 19-23. The alignment guide 210 may include a body 212 and a pivoting assembly 250. The body 212 may include a first end 214 and a second end 216. The body 212 may also include a first opening 218 extending through the first end 214 of the body 212. The first opening 218 may be sized and shaped or configured to receive the guide sleeve 300, as shown in FIGS. 24-30. The guide sleeve 300 may be secured to the body 212, once a desired position is achieved, with at least one set screw 248, as shown in FIGS. 19-26, inserted into openings that extend from an exterior surface into the first opening 218.

Figure 22:
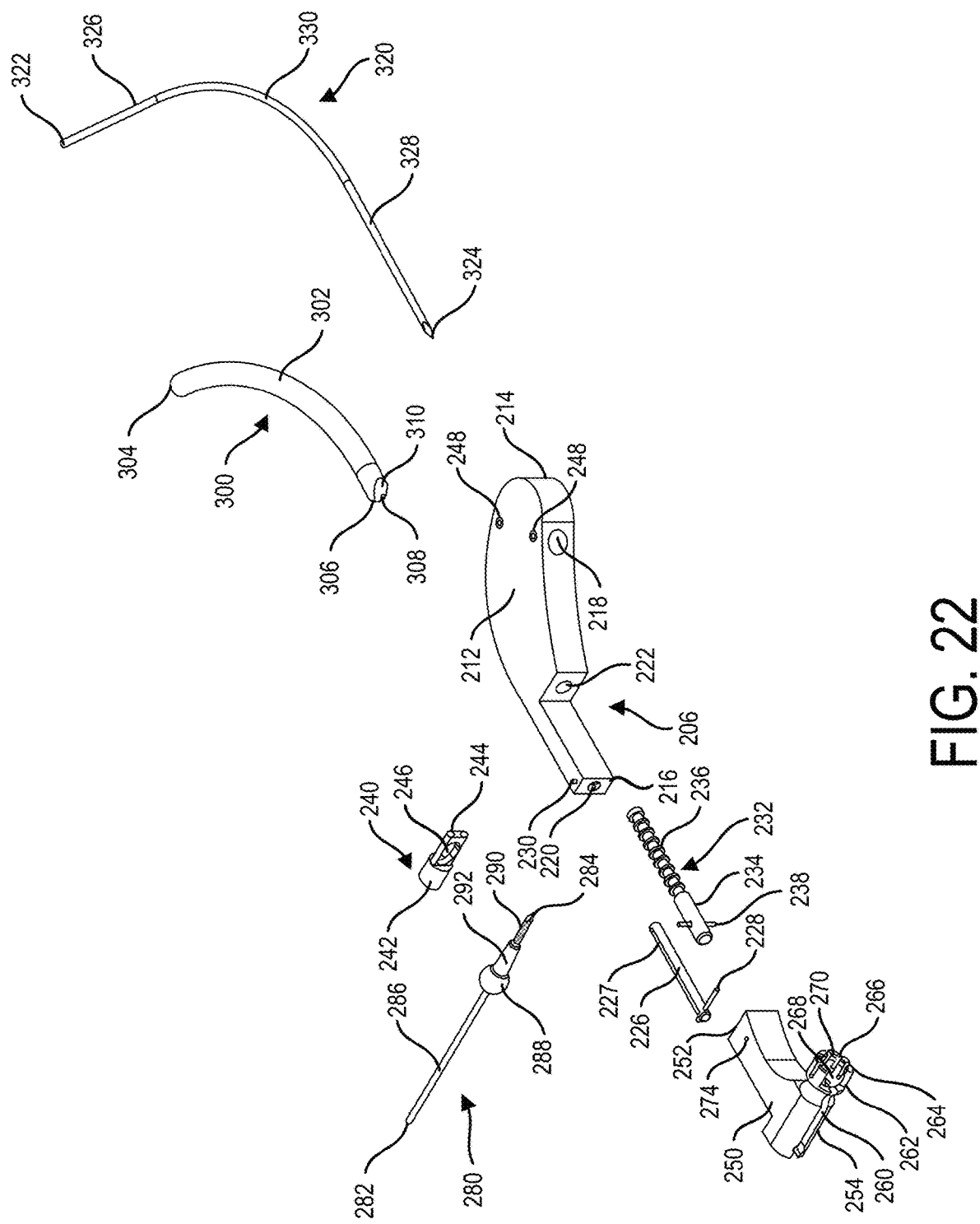
FIG. 22 is an exploded second end perspective view of the bone fixation system of FIG. 19, in accordance with an aspect of the present disclosure.
Figure 23:
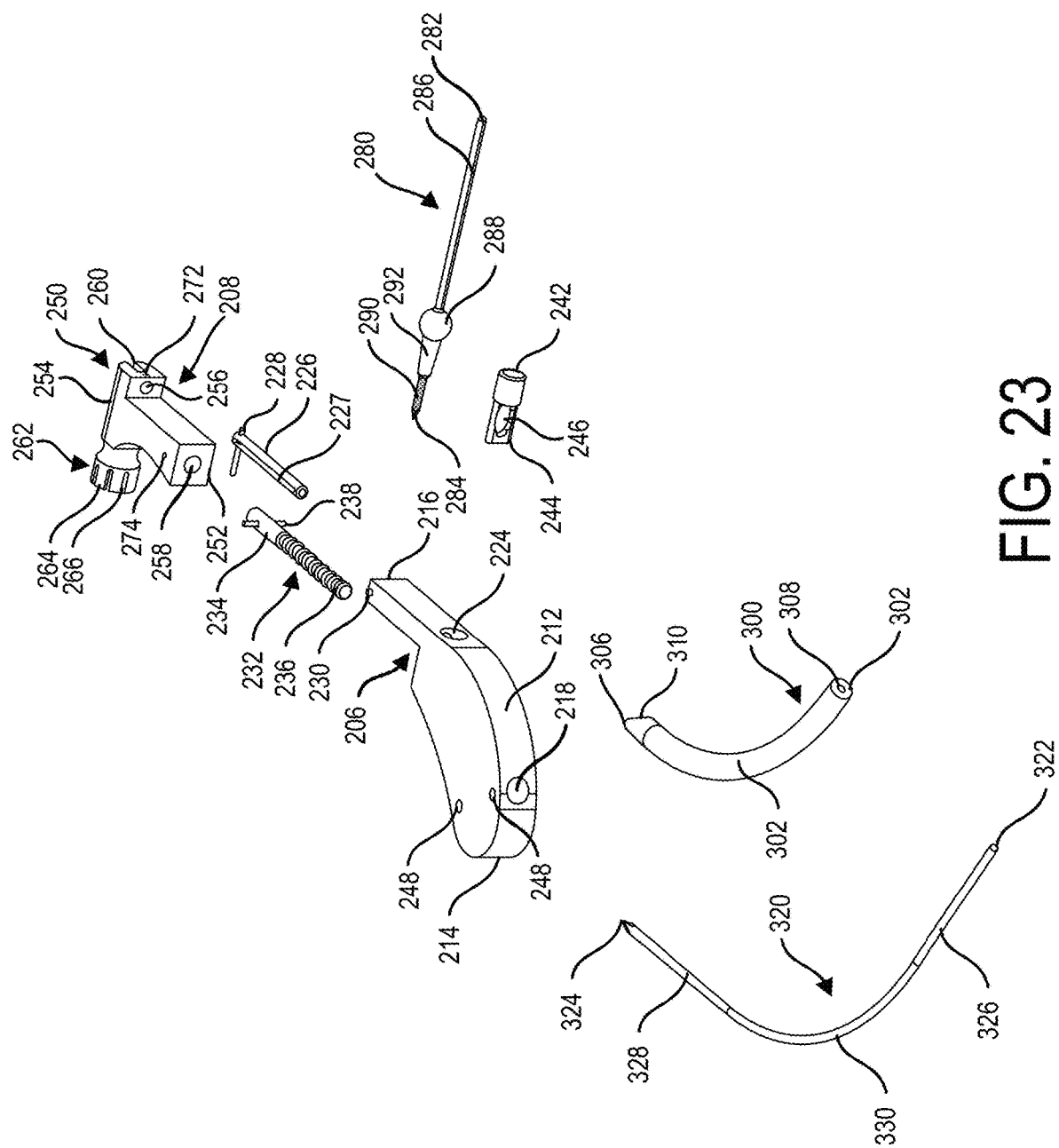
FIG. 23 is an exploded first end perspective view of the bone fixation system of FIG. 19, in accordance with an aspect of the present disclosure.
Figure 24:
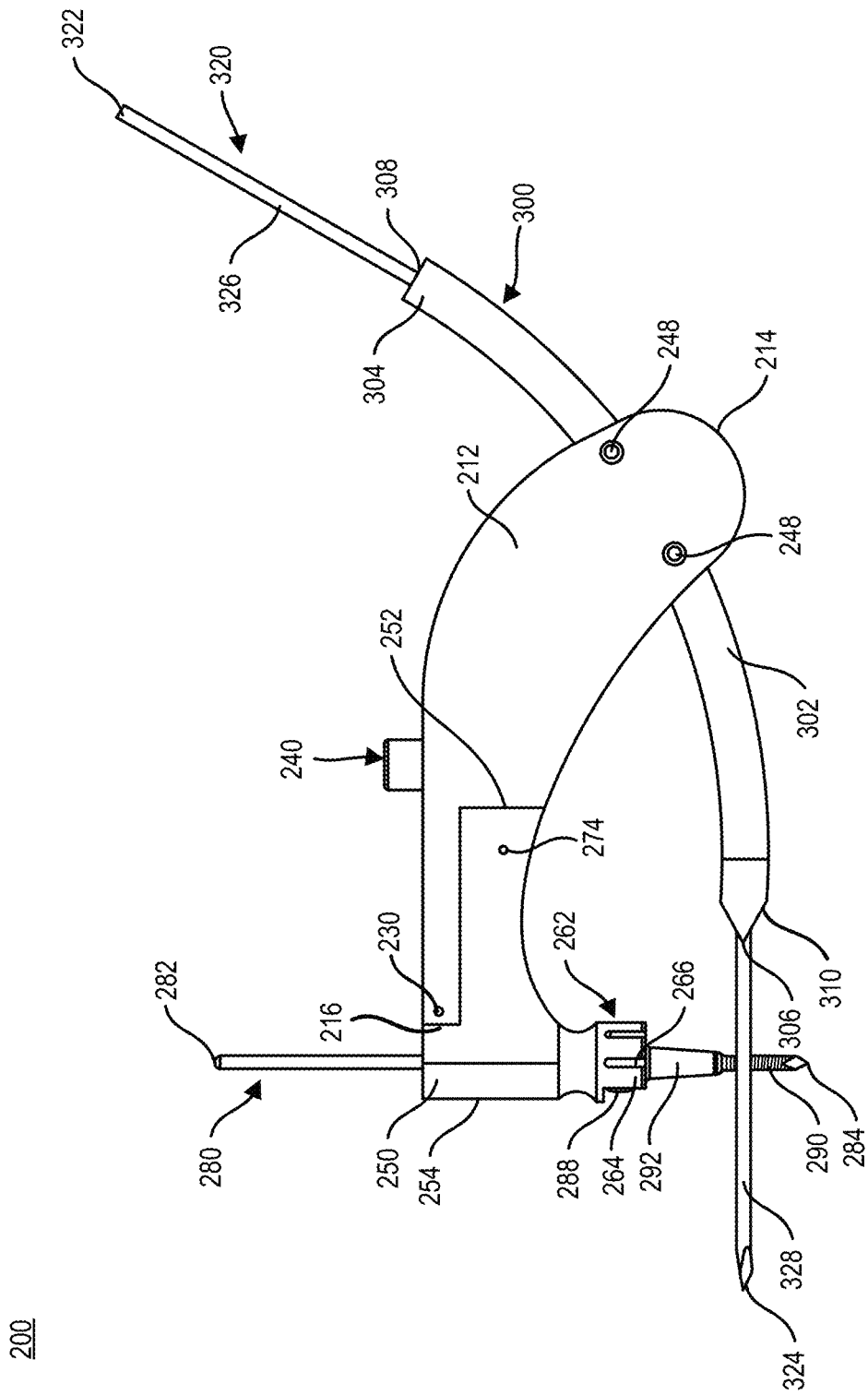
FIG. 24 is a first side view of the bone fixation system of FIG. 19, in accordance with an aspect of the present disclosure.
Figure 25:
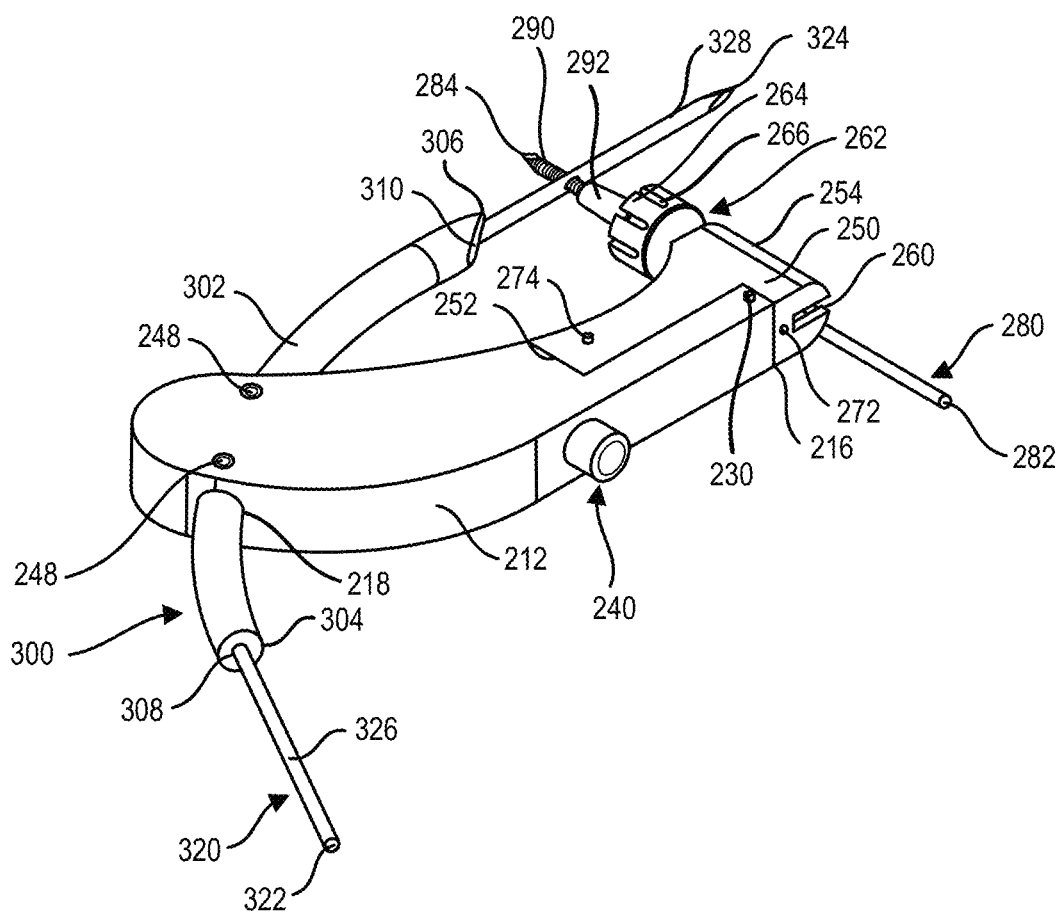
FIG. 25 is a first end perspective view of the bone fixation system of FIG. 19, in accordance with an aspect of the present disclosure.

The second end 216 of the body 212 may include a stepped portion 206, as shown in FIGS. 22 and 23. The stepped portion 206 may include a second opening 220 and a third opening 222 extending into the body 212 in a direction along the length of the body 212, as shown in FIG. 22. The second opening 220 may extend into the first step of the stepped portion 206 and be sized and shaped or configured to receive a portion of a translating member 226. The body 212 may also include a fifth opening 230 extending from a superior surface of the body 212 into the second opening 220. The fifth opening 230 may receive a pin or fastener (not shown) which may extend through the translating member 226, as shown in FIGS. 22 and 23. The translating member 226 may include a slot 227 extending along the length of the translating member 226. The pin extending through the fifth opening 230 may extend through the slot 227 allowing for the pivoting assembly 250 to translate in a proximal-distal direction with respect to the body 212. In addition, the translating member 226 may include an opening for receiving a pin 228 to secure the translating member 226 to the pivoting assembly 250.

The third opening 222 may extend into the second step of the stepped portion 206 and be sized and shaped or configured to receive a portion of a locking member 232. The locking member 232 may include a coupling portion 234 at a first end and a groove portion 236 at a second end, as shown in FIGS. 22 and 23. The coupling portion 234 may also include an opening for receiving a pin 238 to secure the coupling portion 234 of the locking member 232 to the pivoting assembly 250.

The stepped portion 206 may further include a fourth opening 224, as shown in FIG. 23. The fourth opening 224 may extend from a side of the body 212 through the second opening 220 and the third opening 222. The fourth opening 224 may be sized and shaped or configured to receive an engagement button or locking button 240, as shown in FIGS. 22 and 23. The engagement button 240 may include a head portion 242 coupled to a base member 244, as shown in FIGS. 22 and 23. The base member 244 may also include an engagement or locking opening 246. The locking member 232 may be positioned to extend through the locking opening 246. The locking opening 246 may engage at least one of the grooves in the grooved portion 236 of the locking member 232 when in the secured position. In order to translate the pivoting assembly 250 relative to the body 212, the engagement button 240 may be depressed and the pivoting assembly 250 may be moved relative to the body 212. Once the desired position of the body 212 and pivoting assembly 250 is achieved, the engagement button 240 may be released and the opening 246 may engage the grooves of the groove portion 236.

Referring now to FIGS. 22 and 23, the pivoting assembly 250 may include a first end 252 and a second end 254. The pivoting assembly 250 may also include a stepped portion 208 corresponding to the stepped portion 206 of the body 212. The first step of the stepped portion 208 may include a first opening 256 extending into the pivoting assembly 250, as shown in FIG. 23. The first opening 256 may be sized and shaped or configured to receiving a portion of the translating member 226. In addition, the second stepped portion 208 of the pivoting assembly 250 includes a second opening 258 extending into the pivoting assembly 250. The second opening 258 may be sized and shaped or configured to receive a portion of the translating member 226. The pivoting assembly 250 may also include a third opening 272 extending from an exterior surface of the side into the opening 256. The third opening 272 may receive a pin 228 to secure the translating member 226 to the pivoting assembly 250. The pivoting assembly 250 may also include a fourth opening 274 extending from a superior surface into the second opening 258. The fourth opening 274 may receive a pin 238 to secure the locking member 232 to the pivoting assembly 250.

Figure 19:
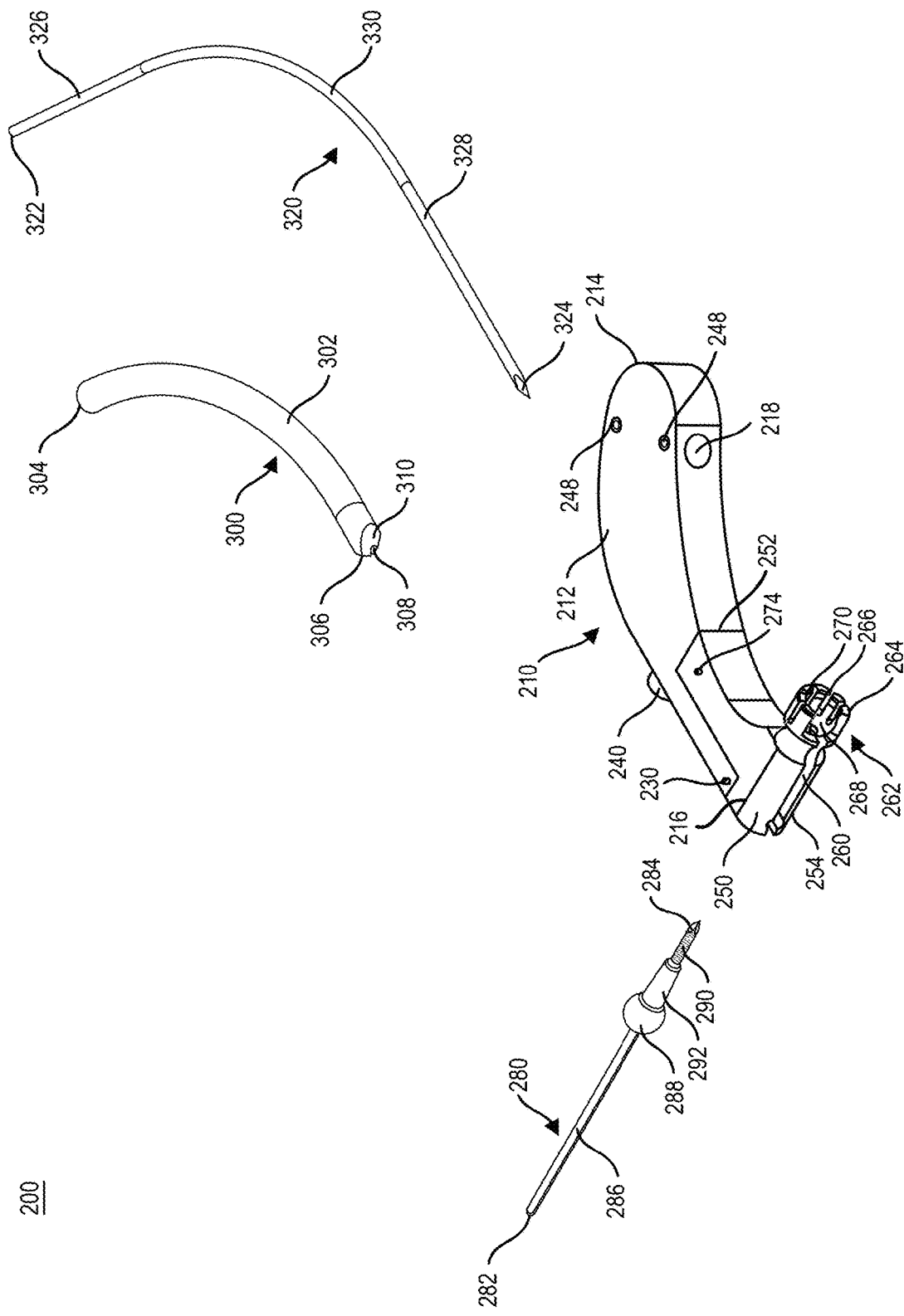
FIG. 19 is a partially exploded second end perspective view of another bone fixation system, in accordance with an aspect of the present disclosure.
Figure 20:
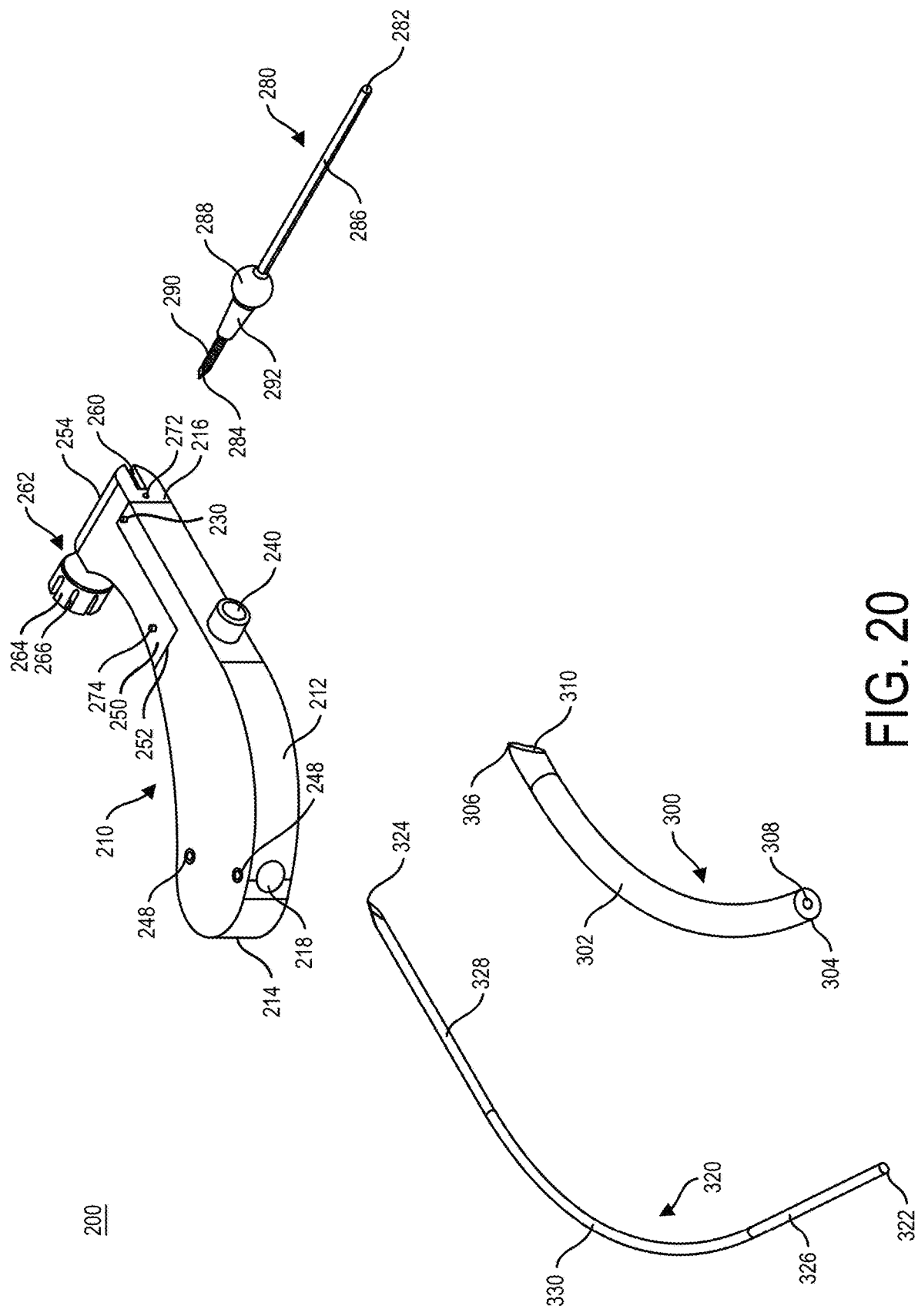
FIG. 20 is a partially exploded first end perspective view of the bone fixation system of FIG. 19, in accordance with an aspect of the present disclosure.
Figure 21:
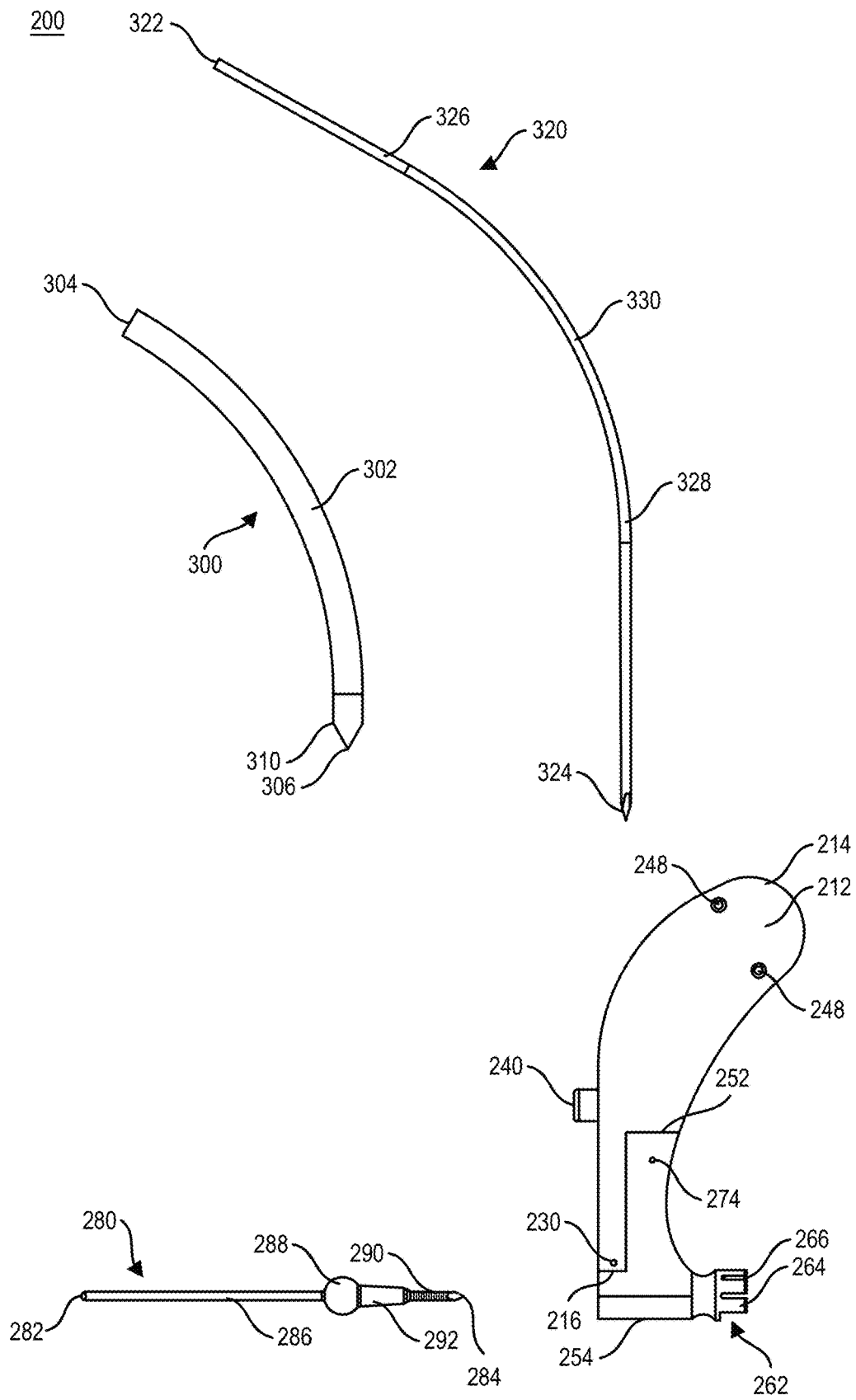
FIG. 21 is a partially exploded first side view of the bone fixation system of FIG. 19, in accordance with an aspect of the present disclosure.
Figure 26:
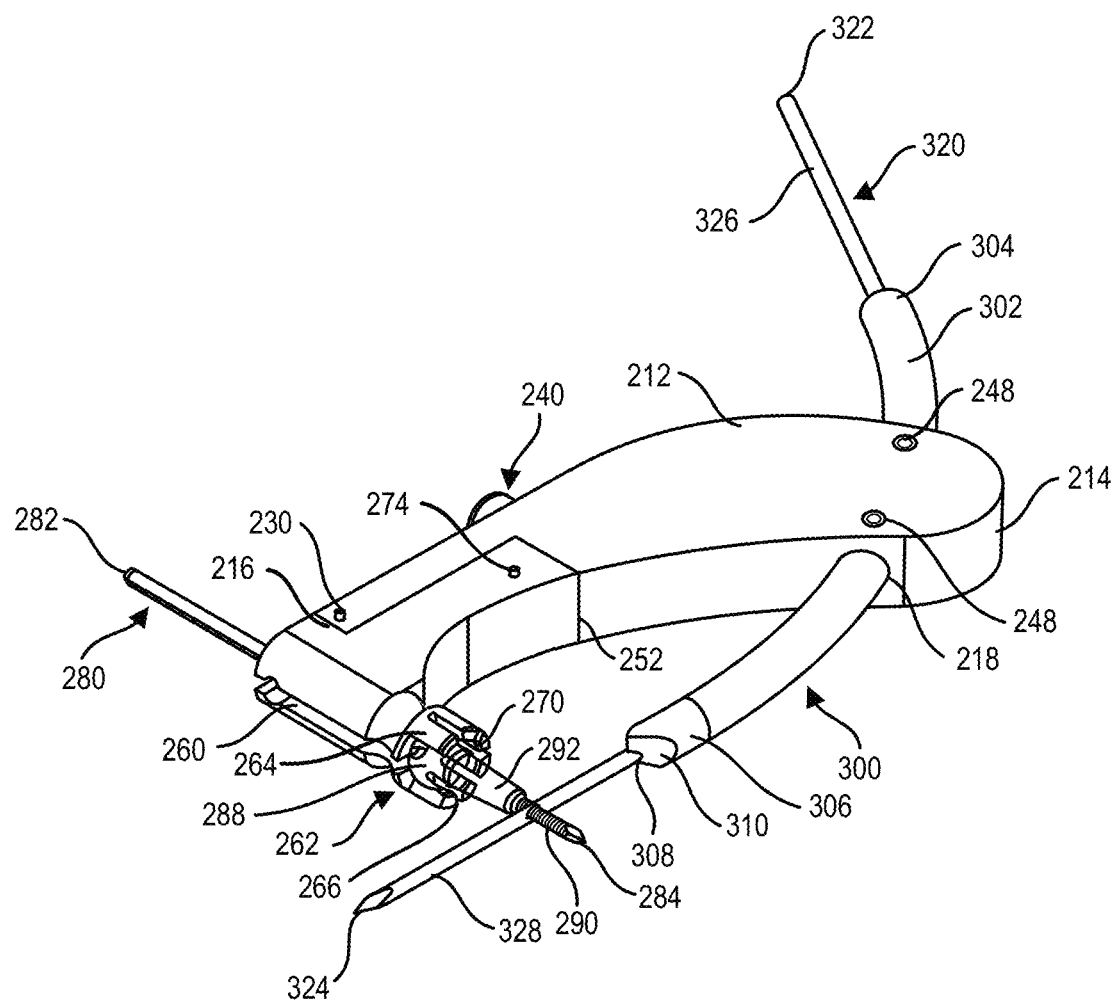
FIG. 26 is a second end perspective view of the bone fixation system of FIG. 19, in accordance with an aspect of the present disclosure.
Figure 27:
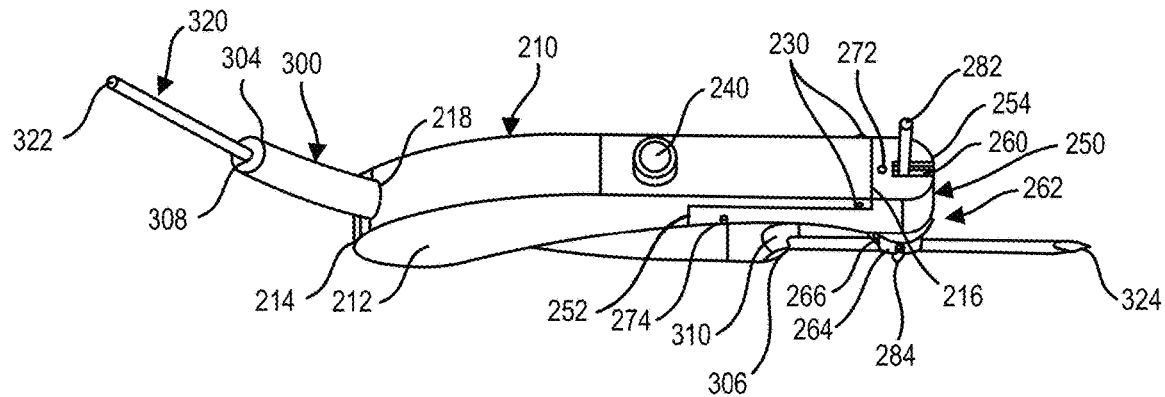
FIG. 27 is a top perspective view of the bone fixation system of FIG. 19, in accordance with an aspect of the present disclosure.
Figure 28:
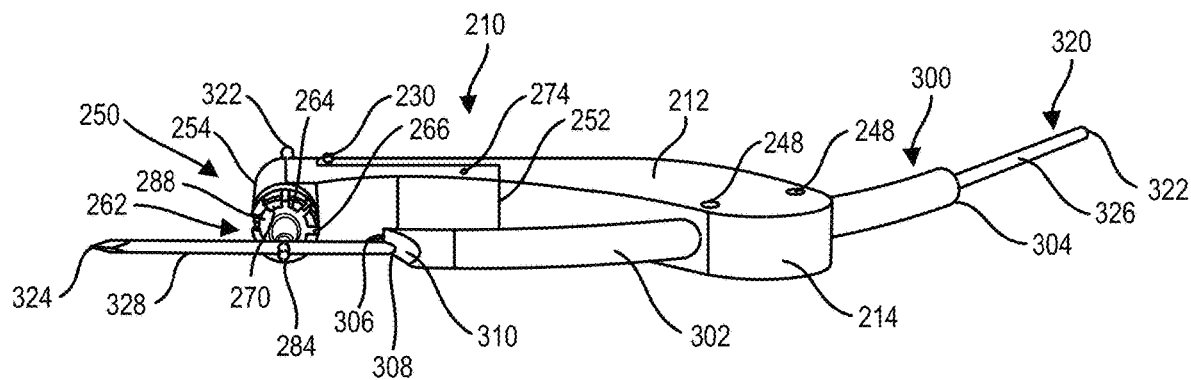
FIG. 28 is a bottom perspective view of the bone fixation system of FIG. 19, in accordance with an aspect of the present disclosure.
Figure 29:
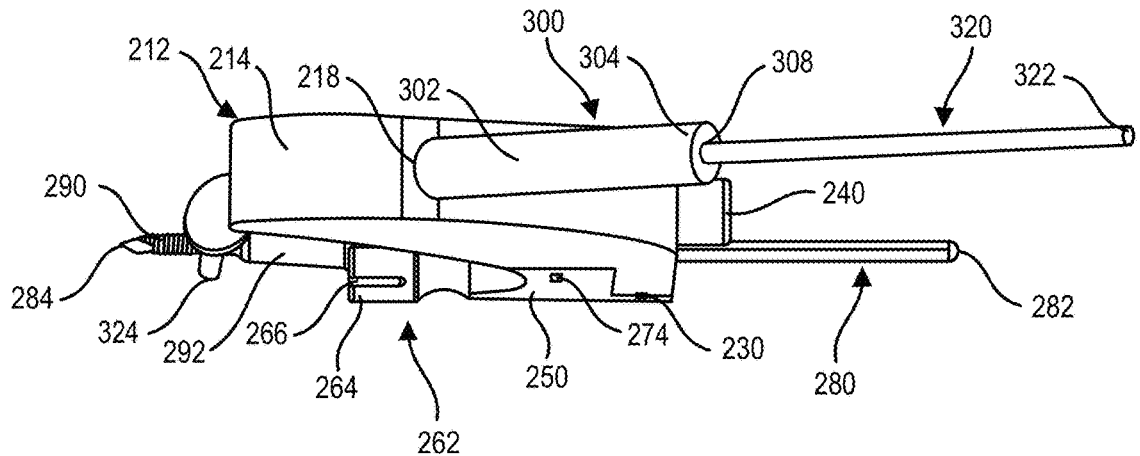
FIG. 29 is a first end view of the bone fixation system of FIG. 19, in accordance with an aspect of the present disclosure.
Figure 30:
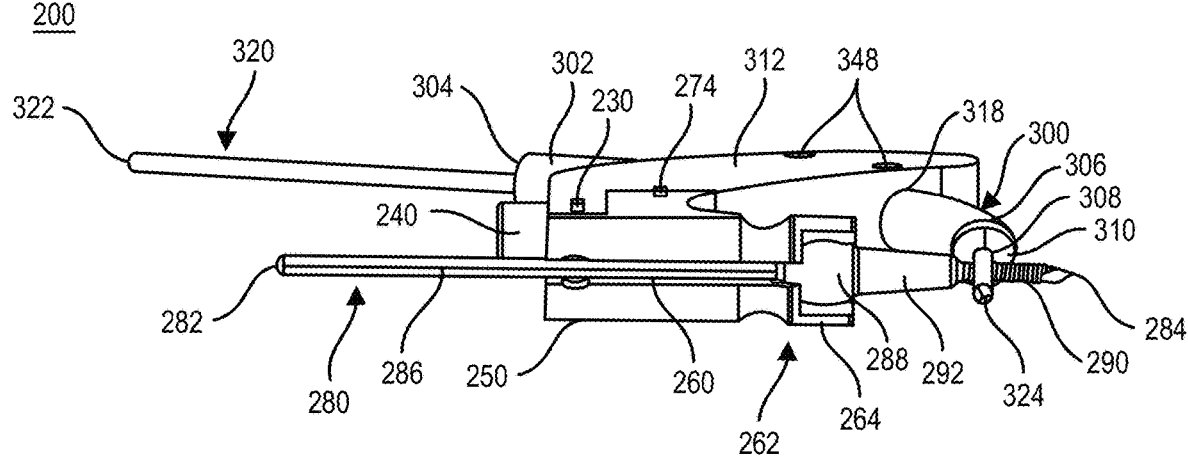
FIG. 30 is a second end view of the bone fixation system of FIG. 19, in accordance with an aspect of the present disclosure.
Figure 31:
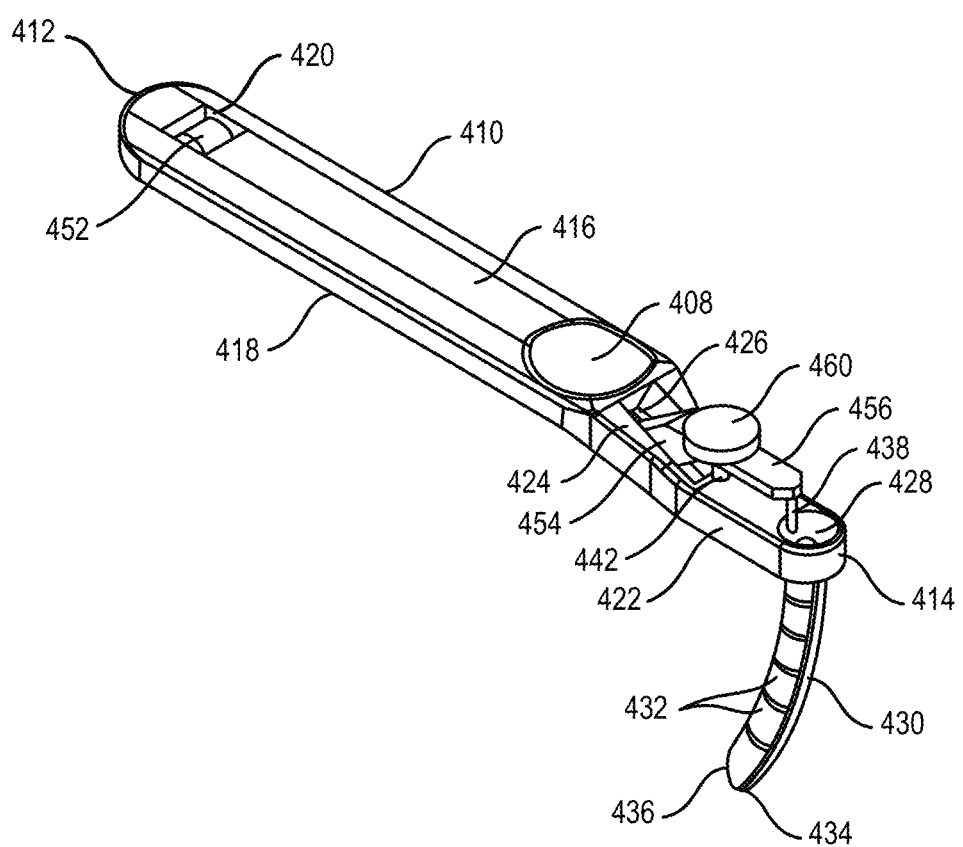
FIG. 31 is a top perspective view of another insertion guide, in accordance with an aspect of the present disclosure.
Figure 32:
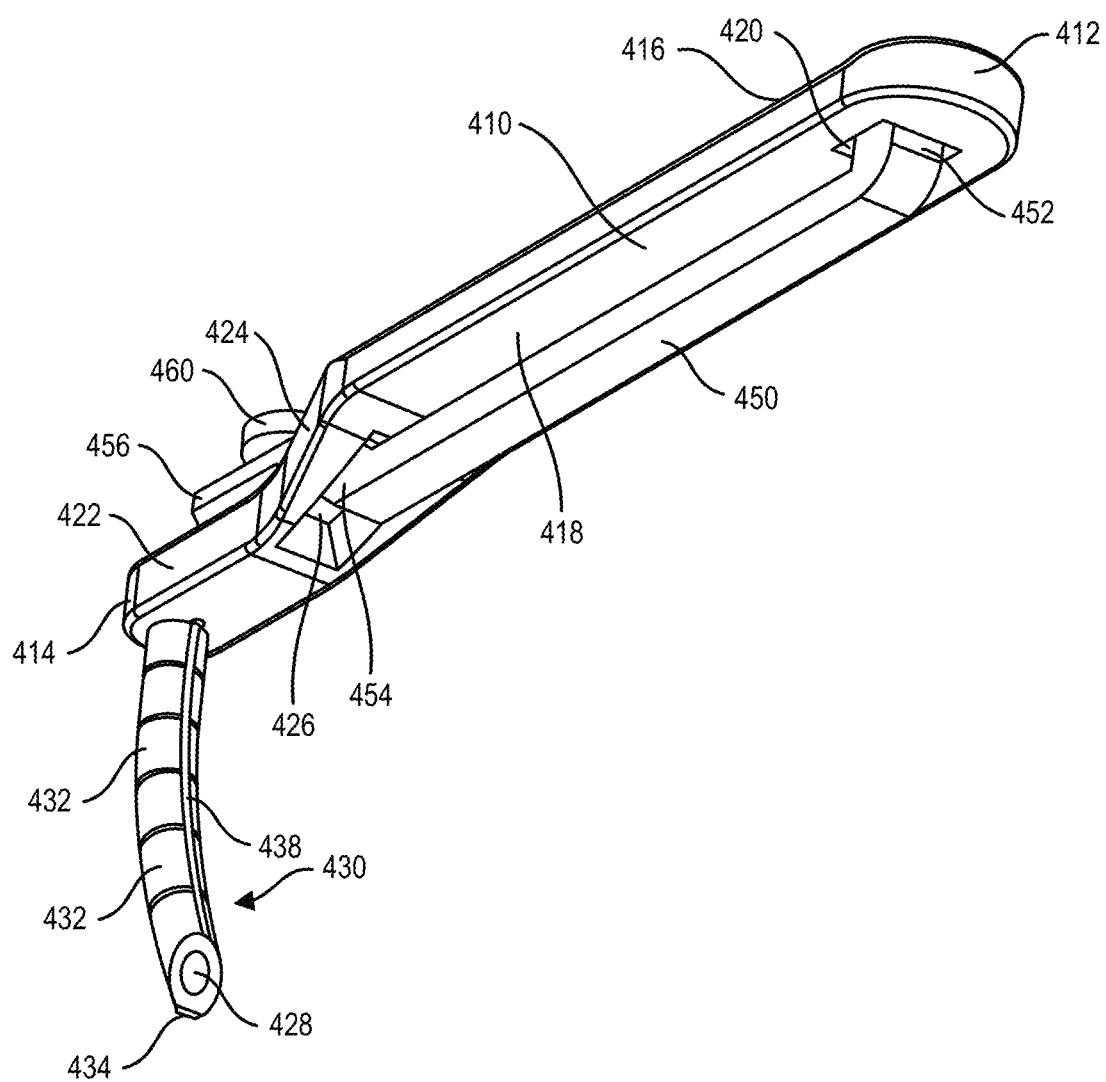
FIG. 32 is a bottom perspective view of the insertion guide of FIG. 31, in accordance with an aspect of the present disclosure.
Figure 33:
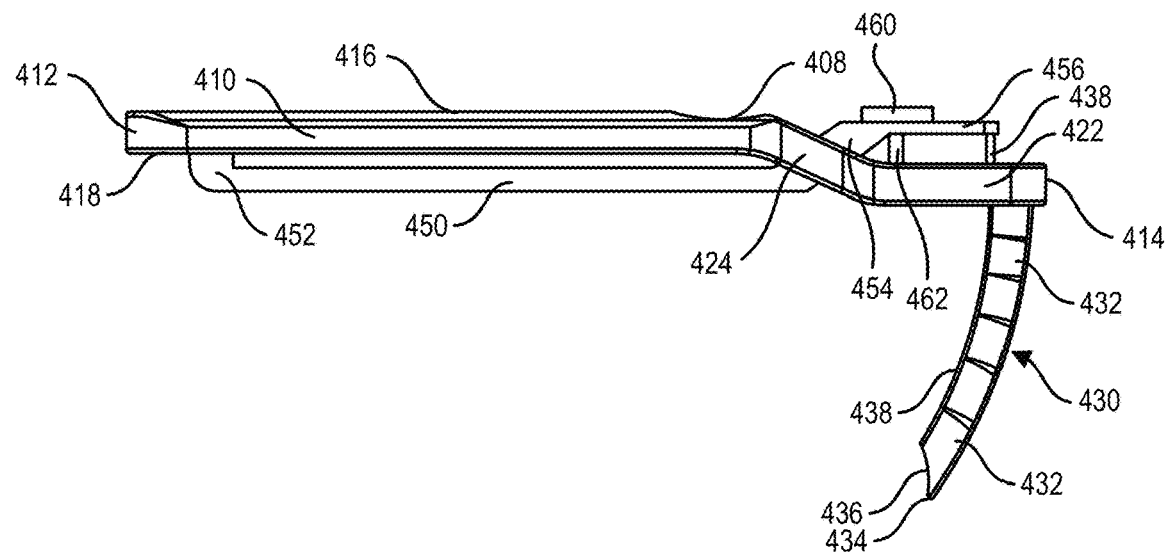
FIG. 33 is a first side view of the insertion guide of FIG. 31, in accordance with an aspect of the present disclosure.
Figure 34:
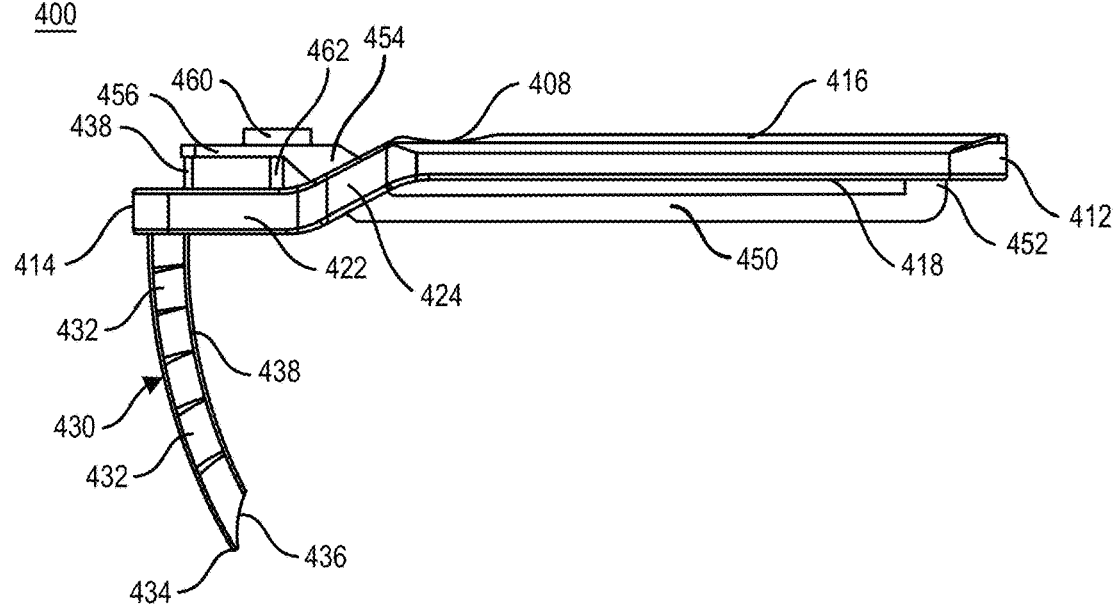
FIG. 34 is a second side view of the insertion guide of FIG. 31, in accordance with an aspect of the present disclosure.
Figure 35:
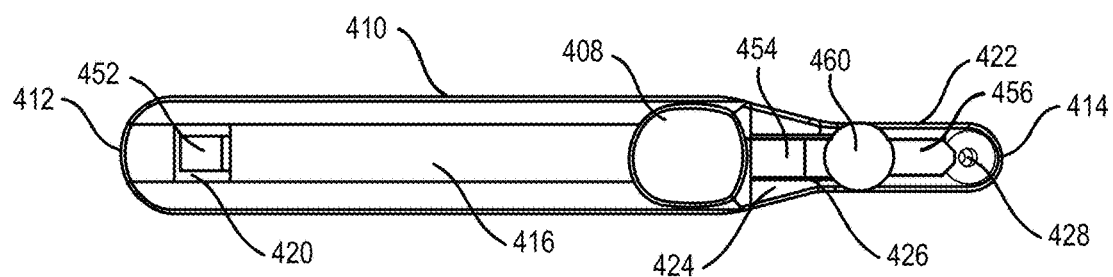
FIG. 35 is a top view of the insertion guide of FIG. 31, in accordance with an aspect of the present disclosure.
Figure 36:
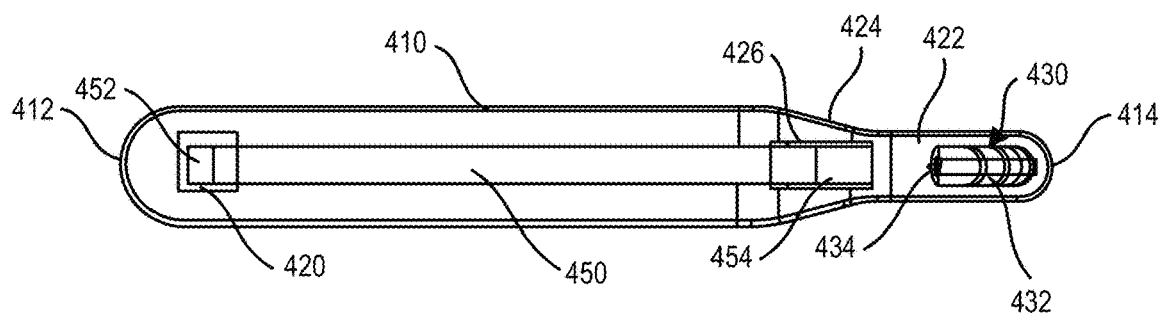
FIG. 36 is a bottom view of the insertion guide of FIG. 31, in accordance with an aspect of the present disclosure.
Figure 38:
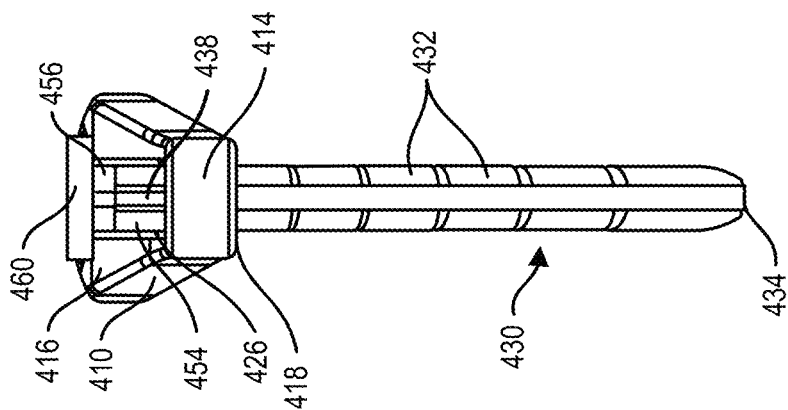
FIG. 38 is a second end view of the insertion guide of FIG. 31, in accordance with an aspect of the present disclosure.
Figure 37:
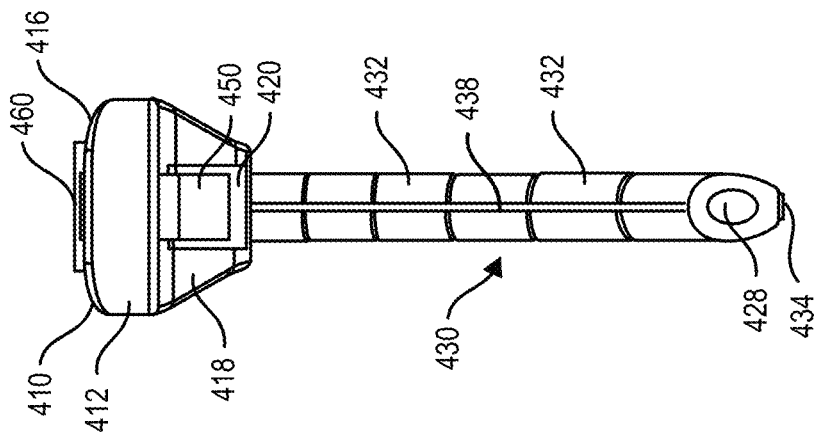
FIG. 37 is a first end view of the insertion guide of FIG. 31, in accordance with an aspect of the present disclosure.

The second end 254 of the pivot assembly 250 may include a pivot slot 260 and a pivoting end 262 for receiving the pivoting member 280. Although not shown, it is contemplated that the pivot slot 260 may be angled, for example, along the longitudinal axis of the alignment guide 210. The pivoting end 262 may include, for example, a plurality of teeth, flanges, protrusions, or extension members 264 alternating with a plurality of grooves or reliefs 266 around the circumference of the pivoting end 262. Each of the plurality of teeth 264 may be, for example, curved on the interior surface of the pivoting end 262 to form at least one curved region 268. The at least one curved region 268 on each of the plurality of teeth 264 may form a spherical opening or opening with a circular or round cross-section on the interior surface of the pivoting end 260. The plurality of teeth 264 may also include, for example, a projection or extension 270 positioned near an end of the pivoting assembly 250 and extending into the spherical opening formed by the curved regions 268 of the teeth 264. The projections 270 provide a retaining surface for coupling the pivoting member 280 to the alignment guide 210, as shown in FIGS. 19, 22, and 26.

The pivoting member 280 may include a first end 282 and a second end 284, as shown in FIGS. 19-23. The terms "pivoting member," "sphere wire," "grip wire," and "alignment wire" may be used interchangeably herein as each essentially refer to a wire including a protrusion. The pivoting member 280 may also include a wire portion 286 extending from the first end 282 to a pivot protrusion or spherical member 288. The pivot protrusion 288 may be, for example, spherical or may have a circular or round cross-section and be sized and shaped to match the opening between the plurality of teeth 264 of the pivoting end 262. The pivot protrusion 288 may rotate within the plurality of teeth 264 in the pivoting end 262. The pivoting member 280 may also include an insertion end 290 and a tapered region 292 extending between the pivot protrusion 288 and the insertion end 290. The insertion end 290 may have a pointed tip for insertion through the skin and into the patient's foot. The pivot protrusion 288 allows for the insertion end 290 to be inserted into the patient's foot at the desired position and at a desired angle relative to the patient's bone.

As shown in FIGS. 19-23, the guide sleeve insert 300 may have a body 302 with a first end 304 and a second end 306. The guide sleeve insert 300 may also include a through hole or cannulation 308 extending from the first end 304 to the second end 306. The guide sleeve insert 300 may also include a bone contacting surface 310 at the second end 306. The bone contacting surface 310 may engage the bone for receiving the guide wire 320. The body 302 may be, for example, curved from the first end 304 to the second end 306.

With continued reference to FIGS. 19-23, the guide wire, k-wire or alignment wire 320 may include a first end 322 and a second end 324. The guide wire 320 may be a straight wire made of a flexible or deformable material, for example, nitinol, to allow the guide wire 320 to bend as the wire 320 follows the through hole 308 through the guide sleeve insert 300. Once inserted into the through hole 308, the guide wire 320 may deform to the shape of the guide wire sleeve 300, as shown in FIGS. 19-22, and include a first wire portion 326 near the first end 322 and a second wire portion 328 near the second end 324. The guide wire 320 may further include a curved portion 330 positioned between the first wire portion 326 and the second wire portion 328 when inserted into the guide sleeve 300.

The method of using the bone fixation system 200 may include obtaining a bone fixation system 200 and making an incision in the patient over the fractured bone. Next, a pivoting member 280 may be placed through the skin and into the patient's bone, for example, a fifth metatarsal bone. The pivoting member 280 should be placed with the insertion end 284 extending through the central axis of the bone. The pivoting member 280 may be placed to position the tip or second end 284 of the pivoting member 280 or the threaded insertion end 290 of the pivoting member 280 along the axis of the trajectory of the k-wire 320, as shown in FIGS. 24-30. Once the pivoting member 280 is inserted in the desired position, the alignment guide 210 may be coupled to the pivoting member 280. The alignment guide 210 may be coupled by engaging the pivoting end 262 of the alignment guide 210 with the pivot protrusion 288 of the pivoting member 280. Then, the opening 218 of the first end 214 of the alignment guide 210 may be positioned to align with the central axis of the bone. The first end 214 may be aligned prior to or after insertion of the guide sleeve 300 into the opening 218. The bone contact surface 310 of the second end 306 of the guide sleeve 300 may then be placed on the patient's bone at the desired entry point for the k-wire 320. After the insertion point has been selected, the k-wire 320 may be inserted into the cannulation 308 at the first end 304 of the guide sleeve 300. The k-wire 320 may be guided through the cannulation 308 and into the patient's bone, for example, into the central axis and in line with the insertion end 290 of the pivoting member 280. After confirming the k-wire 320 is in the desired position, the alignment guide 210 and pivoting member 280 may be removed from the patient. Next, a fastener, for example, fastener 180, as shown in FIG. 1, may be inserted over the k-wire 320 and into an intramedullary canal of the patient, for example, into the central axis of the fifth metatarsal. Once the fastener (not shown) is inserted into the patient's bone, the k-wire 320 may be removed from the patient's bone. Finally, the procedure may be completed and the patient's incision closed.

Referring now to FIGS. 31-38, another insertion guide 400 is shown. The insertion guide 400 includes a handle 410, a guide member 430, and a curvature adjustment member 450. The handle 410 may include a first end 412 opposite the second end 414 and a first surface 416 opposite a second surface 418. The handle 410 may also include a first opening 420 positioned near the first end 412. In addition, the handle 410 may include an alignment member 422 at the second end 414 of the handle 410. The handle 410 may also include a neck portion 424 connecting the body of the handle 410 with the alignment member 422. The handle 410 may further include a second opening 426 positioned in the neck portion 424 of the insertion guide 400. The second end 414 may also include an alignment hole 428 extending through the alignment member 422 and the guide member 430. The guide member 430 may be coupled to the second surface 418 of the alignment member 422 below the alignment hole 428. The handle 410 may also include a depression or finger engagement surface 408 positioned on the first surface 416 of the handle 410 near the neck portion 424.

As shown in FIGS. 31-34, 37 and 38, the guide member 430 may include a plurality of guide member segments 432 coupled together on at least one side. The guide member 430 may also include a pulling member 438 coupled to and extending through the guide member segments 432. A first end of the pulling member 438 may be coupled to the curvature adjustment member 450. The guide member 430 may also include a tip 434 at an end opposite the end of the guide member 430 coupled to the alignment member 422. In addition, the guide member 430 may include a bone contacting surface 436 extending from the tip 434 toward the alignment member 422. The bone contacting surface 436 may be, for example, curved or angled to correspond to the shape of the portion of the bone that will be contacted.

The curvature adjustment member 450 of the guide member 430 may include a tab 452 at a first end, as shown in FIGS. 31, 32, 35 and 36. The tab 452 may extend through the first opening 420 in the handle 410. The curvature adjustment member 450 may also include a neck 454 at a second end of the member 450. The neck 454 may extend through the second opening 426 in the handle 410. The curvature adjustment member 450 may further include a coupling section 456 extending from the neck 454 and positioned above the top surface 416 of the alignment member 422. The curvature adjustment member 450 also includes a locking member and/or fine adjustment member 460. The member 460 may include a projection or shaft 462 that engages an opening (not shown) in the coupling section 456. The member 460 may be turned to lock the curvature adjustment member 450 to the alignment member 422 of the handle 410. By locking the curvature adjustment member 450, the selected curvature of the guide member 430 is secured. In addition, the member 460 may be used to make fine or small adjustments of the curvature of the guide member 430.

A method of using the insertion guide 400 may include determining the desired curvature of the guide member 430 and pressing the tab 452 to activate the pulling member 438. The tab 452 may be depressed until the desired curvature is created in the guide member 430 by the pulling member 438. Once the desired curvature is achieved, the locking member 460 may be tightened to secure the curvature adjustment member 450 and in turn secure the curvature of the guide member 430. If necessary, the locking member 460 may be loosened or tightened to provide for additional fine tuning of the curvature of the guide member 430. After the desired curvature of the guide member 430 is set, the insertion guide 400 may be aligned with the patient's bone and a k-wire, such as, flexible or deformable k-wire 160, 320 may be inserted through the alignment hole 428 and into the patient's bone. The position of the k-wire (not shown) may then be confirmed and if in the desired position, a fastener, such as, fastener 180 as shown in FIG. 1, may be inserted over the k-wire (not shown) and into the patient's bone, as described in greater detail above. After the fastener is inserted into the patient's bone, the k-wire (not shown) may be removed from the patient. Finally, the procedure may be completed and the incision closed.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. A bone fixation system, comprising:
an insertion guide comprising:
a handle member having a first end and a second end, the handle member comprising:
a body disposed at the first end of the handle member; and
an alignment member extending from a portion of the body to the second end of the handle member, the alignment member forming an oblique first angle relative to the body; and
a guide member coupled to the second end of the handle member, wherein the guide member is curved substantially toward the body of the handle member;
a guide wire, wherein the guide member has a through hole for receiving the guide wire; and
a fastener with a cannulation for receiving the guide wire.

2. The bone fixation system of claim 1, wherein the guide member is curved relative to the longitudinal axis of the handle member.

3. The bone fixation system of claim 2, wherein the guide member is curved at a second angle.

4. The bone fixation system of claim 3, wherein the handle member further comprises:
a neck coupled to the body on a first end and the alignment member on a second end.

5. The bone fixation system of claim 4, wherein sides of the neck are at least one of tapered and curved from the body to the alignment member.

6. The bone fixation system of claim 5, wherein the body has a first width and the alignment member has a second width, and wherein the first width is larger than the second width.

7. The bone fixation system of claim 3, wherein the alignment member comprises:
an attachment portion positioned at the second end; and
an opening extending through the attachment portion from a first surface to a second surface.

8. The bone fixation system of claim 7, wherein the guide member comprises:
a body with a first end and a second end; and
a cannulation extending from the first end to the second end.

9. The bone fixation system of claim 8, wherein the body comprises:
an engagement portion at the first end; and
a bone contacting member at the second end, wherein the cannulation is curved from the first end to the bone contact member and the cannulation extends straight through the bone contact member;
wherein the engagement portion is received within and coupled to the opening of the alignment member.

10. The system of claim 7, wherein the guide member comprises a radius of curvature corresponding to the length of the alignment member from the oblique first angle to the opening.

11. The bone fixation system of claim 1, wherein the guide member has a bone contacting surface and the bone contacting surface is shaped to correspond to an exterior surface of a metatarsal bone.

12. The bone fixation system of claim 1, wherein the guide wire comprises:
   a first wire portion; and
   a second wire portion coupled to the first wire portion, wherein the first wire portion is curved relative to the second wire portion when inserted into the guide member.

13. An insertion guide, comprising:
   a handle member with a first end and a second end, the handle member comprising:
      a body disposed at the first end of the handle member;
      an alignment member extending from a portion of the body to the second end of the handle member, wherein the alignment member forms an oblique first angle with the body;
   a guide member coupled to the second end of the handle member; and
   wherein the guide member is curved substantially toward the body of the handle member.

14. The insertion guide of claim 13, wherein the guide member is curved at a second angle.

15. The insertion guide of claim 13, wherein the handle member further comprises:
   a neck coupled to the body on a first end and the alignment member on a second end.

16. The insertion guide of claim 13, wherein the alignment member comprises:
   an attachment portion positioned at the second end; and
   an opening extending through the attachment portion from a first surface to a second surface.

17. The insertion guide of claim 16, wherein the guide member comprises:
   a body with a first end and a second end; and
   a cannulation extending from the first end to the second end.

18. The insertion guide of claim 17, wherein the body comprises:
   an engagement portion at the first end; and
   a bone contacting member coupled to the body at the second end, wherein the cannulation is curved from the first end to the bone contacting member and the cannulation extends straight through the bone contacting member;
   wherein the engagement portion is received within and coupled to the opening of the alignment member.

19. A method of using a bone fixation system for fixation of a metatarsal, comprising:
   creating an incision near the metatarsal;
   aligning a guide member of an insertion guide with a central axis of the metatarsal;
   inserting an alignment wire through the guide member and into the central axis of the metatarsal such that the alignment wire extends into the metatarsal along the central axis thereof;
   removing the insertion guide from the alignment wire;
   inserting a fastener over the alignment wire and into the central axis of the metatarsal such that the fastener is positioned to cross a fracture of the metatarsal;
   removing the alignment wire from the metatarsal; and
   closing the incision.

\* \* \* \* \*